United States Patent
Prentice et al.

(10) Patent No.: US 10,155,177 B2
(45) Date of Patent: Dec. 18, 2018

(54) ELECTROMECHANICAL AND FLUIDIC INTERFACE TO A MICROFLUIDIC SUBSTRATE

(71) Applicant: Waters Technologies Corporation, Milford, MA (US)

(72) Inventors: David P. Prentice, Millville, MA (US); Russell L. Keene, Sudbury, MA (US); Stanislaw Koziol, Wrentham, MA (US); Joseph D. Michienzi, Plainville, MA (US); Paul E. Linderson, Warwick, RI (US); Gary W. Bertone, Southborough, MA (US)

(73) Assignee: WATERS TECHNOLOGIES CORPORATION, Milford, MA (US)

( * ) Notice: Subject to any disclaimer, the term of this patent is extended or adjusted under 35 U.S.C. 154(b) by 13 days.

(21) Appl. No.: 14/747,074

(22) Filed: Jun. 23, 2015

(65) Prior Publication Data
US 2015/0290644 A1     Oct. 15, 2015

Related U.S. Application Data

(62) Division of application No. 13/202,363, filed as application No. PCT/US2010/026352 on Mar. 5, 2010.
(Continued)

(51) Int. Cl.
*B01D 15/10*     (2006.01)
*B01L 3/00*     (2006.01)
(Continued)

(52) U.S. Cl.
CPC ........ *B01D 15/10* (2013.01); *B01L 3/502715* (2013.01); *B01L 3/502753* (2013.01);
(Continued)

(58) Field of Classification Search
CPC ............... B01D 15/10; B01L 3/502753; B01L 3/502715; B01L 3/563; B05B 1/02;
(Continued)

(56) References Cited

U.S. PATENT DOCUMENTS

| | | |
|---|---|---|
| 4,566,525 A | 1/1986 | Li et al. |
| 5,089,455 A | 2/1992 | Ketcham et al. |

(Continued)

FOREIGN PATENT DOCUMENTS

| | | |
|---|---|---|
| EP | 0964428 A2 | 12/1999 |
| EP | 1470416 A2 | 10/2004 |

(Continued)

OTHER PUBLICATIONS

First Office Action in related Chinese Patent Application No. 201080010751.1, dated Jul. 18, 2013; 12 pages.
(Continued)

*Primary Examiner* — Lore R Jarrett
(74) *Attorney, Agent, or Firm* — Schmeiser, Olsen & Watts LLP

(57) ABSTRACT

A liquid-chromatography module includes a microfluidic cartridge housing a microfluidic substrate with a channel for transporting fluid. The microfluidic substrate has fluidic apertures through which fluid is supplied to the channel. One side of the cartridge has nozzle openings, each aligning with a fluidic aperture in the microfluidic substrate and receiving a fluidic nozzle. A clamping assembly has a plunger that is movable into a clamped position and an end housing that defines a chamber. One wall of the end housing has a fluidic block with fluidic nozzles extending into the chamber. A second wall has a slot through which the cartridge enters the chamber. When moved into the clamped position while the cartridge is in the chamber, the plunger urges the cartridge against the fluidic block such that each fluidic nozzle enters (Continued)

one nozzle opening and establishes fluidic communication with one fluidic aperture in the microfluidic substrate.

7 Claims, 22 Drawing Sheets

Related U.S. Application Data

(60) Provisional application No. 61/158,230, filed on Mar. 6, 2009.

(51) Int. Cl.
| | |
|---|---|
| *G01N 30/60* | (2006.01) |
| *G01N 30/72* | (2006.01) |
| *H01J 49/16* | (2006.01) |
| *G01N 27/447* | (2006.01) |
| *B05B 1/02* | (2006.01) |
| *B05B 1/00* | (2006.01) |

(52) U.S. Cl.
CPC .............. *B01L 3/563* (2013.01); *B05B 1/02* (2013.01); *G01N 27/44791* (2013.01); *G01N 30/6095* (2013.01); *G01N 30/724* (2013.01); *G01N 30/7233* (2013.01); *G01N 30/7266* (2013.01); *H01J 49/167* (2013.01); *B01L 3/5027* (2013.01); *B01L 2200/025* (2013.01); *B01L 2200/027* (2013.01); *B01L 2200/0689* (2013.01); *B01L 2300/0816* (2013.01); *B01L 2300/0883* (2013.01); *B05B 1/00* (2013.01); *G01N 30/72* (2013.01); *Y10T 137/598* (2015.04); *Y10T 436/24* (2015.01)

(58) Field of Classification Search
CPC .... B05B 1/00; G01N 30/7233; G01N 30/724; G01N 27/44791; G01N 30/6095; G01N 30/7266; H01J 49/167; Y10T 137/598; Y10T 436/24

See application file for complete search history.

(56) References Cited

U.S. PATENT DOCUMENTS

| | | | |
|---|---|---|---|
| 5,872,010 A | 2/1999 | Karger et al. | |
| 6,581,441 B1 * | 6/2003 | Paul | G01N 30/6095 210/656 |
| 6,800,849 B2 | 10/2004 | Staats | |
| 6,832,787 B1 | 12/2004 | Renzi | |
| 7,303,727 B1 | 12/2007 | Dubrow et al. | |
| 7,871,575 B2 | 1/2011 | Baeuerle et al. | |
| 2002/0100714 A1 * | 8/2002 | Staats | B01L 3/5027 210/85 |
| 2003/0087454 A1 | 5/2003 | Schultz et al. | |
| 2003/0111599 A1 * | 6/2003 | Staats | H01J 49/0431 250/288 |
| 2003/0156993 A1 * | 8/2003 | Staats | B01L 3/502707 204/455 |
| 2003/0200794 A1 | 10/2003 | Paul | |
| 2003/0224531 A1 | 12/2003 | Brennen | |
| 2004/0045904 A1 | 3/2004 | Zhang et al. | |
| 2005/0158209 A1 | 7/2005 | Bender et al. | |
| 2005/0178960 A1 | 8/2005 | Kameoka et al. | |
| 2006/0019379 A1 | 1/2006 | Taylor et al. | |
| 2006/0193748 A1 | 8/2006 | Tai | |
| 2007/0025887 A1 | 2/2007 | Baeuerle et al. | |
| 2007/0122314 A1 | 5/2007 | Strand et al. | |
| 2008/0235948 A1 | 10/2008 | Bousse et al. | |

FOREIGN PATENT DOCUMENTS

| | | |
|---|---|---|
| EP | 1715348 A1 | 10/2006 |
| JP | 2000162184 A | 6/2000 |
| JP | 2002533231 A | 10/2002 |
| JP | 2002538397 A | 11/2002 |
| JP | 2002538461 A | 11/2002 |
| JP | 2004522596 A | 7/2004 |
| JP | 2004219247 A | 8/2004 |
| JP | 2005517179 A | 6/2005 |
| JP | 2005518936 A | 6/2005 |
| JP | 2007171155 A | 7/2007 |
| JP | 2008516228 A | 5/2008 |
| WO | 0230486 A2 | 4/2002 |
| WO | 03054524 A1 | 7/2003 |
| WO | 2005084191 A2 | 9/2005 |
| WO | 2005096751 A2 | 10/2005 |
| WO | 2007011867 A2 | 1/2007 |
| WO | 2007075293 A | 7/2007 |
| WO | 2007112224 A | 10/2007 |
| WO | 2007131925 A | 11/2007 |
| WO | 2010138667 A1 | 12/2010 |

OTHER PUBLICATIONS

European Search Report in related European Application No. 10749386. 8, dated Oct. 14, 2013; 9 pages.
Office Action in related Japanese patent application No. 2011-553133, mailed on Dec. 3, 2013; 6 pages.
Office Action in related Japanese patent application No. 2011-553134, mailed on Dec. 3, 2013; 8 pages.
Second Office Action in related Chinese Patent Application No. 201080010751.1, dated May 8, 2014; 16 pages.
Notice of Allowance in related Chinese Patent Application No. 201080010752.6, mailed on Mar. 11, 2014; 4 pages.
Decision on Rejection in related Japanese Patent Application No. 2011-553134, mailed on Jan. 6, 2015; 6 pages.
PCT Written Opinion, form ISA/237 for PCT/US2010/026352, dated Apr. 16, 2010; 6 pages.
PCT International Search Report, form ISA/210+220 for PCT/US2010/026352, dated Apr. 16, 2010; 2 pages.
Notice of Allowance in related U.S. Appl. No. 14/273,040, mailed on Oct. 5, 2015; 11 pg.
Extended European Search Report in European Patent Application No. 10749381.9, dated Nov. 14, 2013; 8 pages.
Examination Report in European Patent Application No. 10749381. 9, dated Jul. 5, 2017; 7 pages.
Kim, et al., "Microfabricated PDMS Multichannel Emitter for Electrospray Ionization Mass Spectrometry", Journal of the American Society for Mass Spectrometry, vol. 12, No. 4, Apr. 1, 2001; pp. 463-469, Elsevier Science Inc, U.S., 2001, XP004233064, ISSN: 1044-0305, DOI: 10.1016/S1044-0305(01)00219-7.
Schultz, et al., "A Fully Integrated Monolithic Microchip Electrospray Device for Mass Spectrometry", Analytical Chemistry, vol. 72, No. 17, Sep. 1, 2000, pp. 4058-4063, American Chemical Society, U.S., 2000, XP055021623, ISSN: 0003-2700, DOI: 10.1021/ac000325y.
Office Action in European Patent Application No. 10749386.8, dated Sep. 29, 2017; 6 pages.

* cited by examiner

ELECTROMECHANICAL AND FLUIDIC INTERFACE TO A MICROFLUIDIC SUBSTRATE

RELATED APPLICATIONS

This application is a divisional of U.S. patent application Ser. No. 13/202,363, filed on Oct. 14, 2011, titled "Electrospray Interface to a Microfluidic Substrate", which is a 371 National Stage entry of International Application No. PCT/US10/26352, filed on Mar. 5, 2010 titled "Electromechanical and Fluidic Interface To A Microfluidic Substrate", which claims priority from U.S. Provisional Application Ser. No. 61/158,230, filed Mar. 6, 2009, titled "Liquid Chromatography-Mass Spectrometry Apparatus Having a Microfluidic Substrate," the entireties of which are incorporated herein by reference.

FIELD OF THE INVENTION

The invention relates generally to liquid chromatography-mass spectrometry instruments. More specifically, the invention relates to an electromechanical and fluidic interface to a microfluidic substrate used by such analytical instruments.

BACKGROUND

High-performance liquid chromatography (HPLC) instruments are analytical tools for separating, identifying, and quantifying compounds. Traditional HPLC instruments use analytical columns constructed from stainless-steel tubing. Typically, the tubing has an inner bore diameter of 4.7 mm, and its length ranges from about 5 cm to about 25 cm.

In addition, the analytical column of an HPLC instrument typically has a fritted end fitting attached to a piece of tubing. Particles, typically silica-based, functionalized with a variety of functional moieties, pack the tube.

To achieve optimal separation efficiency, using the completed column, an appropriate flow rate of a mobile phase is important. For a 4.7 mm diameter column packed with 5 μm diameter particles, a desirable flow rate is typically between about 1 mL/min and about 2 mL/min. Minimizing the presence of unswept dead volume in the plumbing of the HPLC instrument is desirable for maintaining separation efficiency.

In an HPLC instrument, an injector is typically used to inject a sample into a flowing mobile phase as a discrete fluidic plug. Dispersion of a plug band as it travels to and/or from the column reduces the ultimate efficiency of the chromatographic system. For example, in a chromatographic system using 4.7 mm column tubing and a mobile phase flowing at 1-2 mL/min, tubing having an outer diameter of 1/16 inch and an inner diameter of about 0.010 inch is typically used to plumb connections between the various HPLC components (e.g. pump, injector, column, and detector). For these flow rates and tubing dimensions, it is relatively easy to machine port details to tolerances that will ensure minimal band broadening at tubing interfaces.

A desire to reduce mobile-phase solvent consumption, in part, has motivated a trend towards reducing column inner diameter. Thus, several scales of chromatography are now commonly practiced; these are typically defined as shown in Table 1 (where ID is inner diameter.)

TABLE 1

| HPLC Scale | Column ID | Typical Flow range |
| --- | --- | --- |
| Analytical | 4.7 mm | 1s mL/min |
| Microbore | 1-2 mm | 100s μL/min |
| Capillary | 300-500 μm | 10s μL/min |
| Nano | 50-150 μm | 100s nL/min |

Microbore HPLC has often been practiced with equipment similar to that used for analytical scale HPLC, with minor modifications. Aside from requiring the exercise of a small degree of additional care in making fittings, microbore HPLC typically requires an operating skill level similar to that of analytical scale HPLC.

In contrast, capillary and nano-scale HPLC require relatively significant changes in HPLC components relative to analytical-scale HPLC. Generation of stable mobile-phase flows of less than about 50 μL/min is relatively difficult using standard open-loop reciprocating HPLC pumps, such as those commonly found in analytical and microbore HPLC systems.

For capillary-scale chromatography, stainless-steel tubing is usable for component interconnections; however, the inner diameter must typically be less than 0.005 inch (less than about 125 μm). Care is generally required in the manufacture of fitting terminations to avoid creation of even minute amounts of dead volume.

For nano-scale chromatography, tubing having inner diameters of about 25-50 μm is typically required to interconnect components of an instrument (e.g., to connect a pump to a separation column). Because stainless-steel tubing is typically unavailable in these dimensions, polyimide-coated fused-silica tubing is typically used. Although fused-silica tubing has excellent dimensional tolerances and very clean, non-reactive interior walls, it is fragile and can be difficult to work with. In addition, interconnection ports should be machined to exacting tolerances to prevent even nanoliters of unswept dead volume.

While the primary motivation to replace analytical-scale HPLC with microbore-scale HPLC may be the desire for reduced solvent consumption, moving to capillary-scale and nano-scale chromatography can support improved detection sensitivity for mass spectrometers, in addition to further reducing solvent consumption, when, for example, flows of less than about 10 μL/min are used. Moreover, capillary-scale or nano-scale systems are often the only options for the sensitive detection typically required for applications involving small amounts of available sample (e.g., neonatal blood screening).

Despite the advantages of capillary-scale and nano-scale chromatography, HPLC users tend to employ microbore-scale and analytical-scale chromatography systems. As described above, these systems typically provide good reliability and relative ease-of-use. In contrast, maintenance of good chromatographic efficiency while operating a capillary-scale or nano-scale chromatographic system requires significant care when plumbing the system (e.g., using tubing to connect pump, injector, column, and detector).

In practice, an operator switching from an analytical or microbore-scale system to a capillary or nano-scale system at times finds that better separation efficiency was achieved with the higher-flow rate (i.e., the analytical or microbore-scale) system. This typically occurs due to insufficiency in the operator's knowledge or experience required to achieve low band-spreading tubing interconnections. Moreover, use of smaller inner-diameter tubing at times can lead to frequent plugging of tubing.

Due the relative difficulty typically encountered with capillary-scale HPLC systems and, even more so, with nano-scale HPLC systems, such systems have primarily been used only when necessary, such as for small sample sizes, and when a relatively skilled operator is available. Thus, analytical laboratories tend to possess more analytical-scale and microbore-scale systems than capillary-scale and nano-scale systems, and do not realize the full benefits available from capillary-scale and nano-scale HPLC.

SUMMARY

In one aspect, the invention features an apparatus comprising a microfluidic substrate with a channel for transporting fluid. A first side of the microfluidic substrate has a plurality of apertures through which fluid can be supplied to the channel. A plurality of fluidic nozzles is disposed adjacent the first side of the microfluidic substrate. Each fluidic nozzle has a fluid-egress end in alignment with and facing one of the apertures in the first side of the microfluidic substrate. A clamping assembly clamps the fluid-egress ends of the fluidic nozzles flush against the first side of the microfluidic substrate with sufficient pressure to establish a leakproof fluidic pathway between each fluidic nozzle and the aperture with which that fluidic nozzle is in alignment.

In another aspect, the invention features an apparatus comprising a microfluidic cartridge housing a substrate with a channel for transporting fluid. A first side of the substrate has a plurality of apertures through which fluid can be supplied to the channel. A clamping assembly includes a housing that defines a chamber for receiving the microfluidic cartridge therein. The housing has a wall from which a plurality of fluidic nozzles extend inwardly into the chamber. Each of the fluidic nozzles aligns with one of the apertures in the first side of the substrate when the microfluidic cartridge is installed at a particular position in the chamber. The clamping assembly clamps the fluidic nozzles flush against the first side of the substrate with sufficient pressure to establish a leakproof fluidic pathway between each fluidic nozzle and the aperture with which that fluidic nozzle is aligned.

In still another aspect, the invention features a microfluidic device comprising a microfluidic substrate having a channel for transporting fluid. A first side of the microfluidic substrate has a high-voltage input port for coupling high voltage to the channel and a plurality of apertures through which fluid is supplied to the channel. Circuitry includes an electrical connector with an array of electrical contacts. Housing encloses the microfluidic substrate and the circuitry. A first side of the housing has a high-voltage input port aligned with the high-voltage input port of the microfluidic substrate, a gas inlet port adapted to receive a gas nozzle, a window aligned with the array of electrical contacts of the circuitry, and a plurality of nozzle openings each aligned with one of the apertures in the microfluidic substrate and adapted to receive a fluidic nozzle.

BRIEF DESCRIPTION OF THE DRAWINGS

The above and further advantages of this invention may be better understood by referring to the following description in conjunction with the accompanying drawings, in which like numerals indicate like structural elements and features in various figures. The drawings are not necessarily to scale, emphasis instead being placed upon illustrating the principles of the invention.

DETAILED DESCRIPTION

Figure 1:
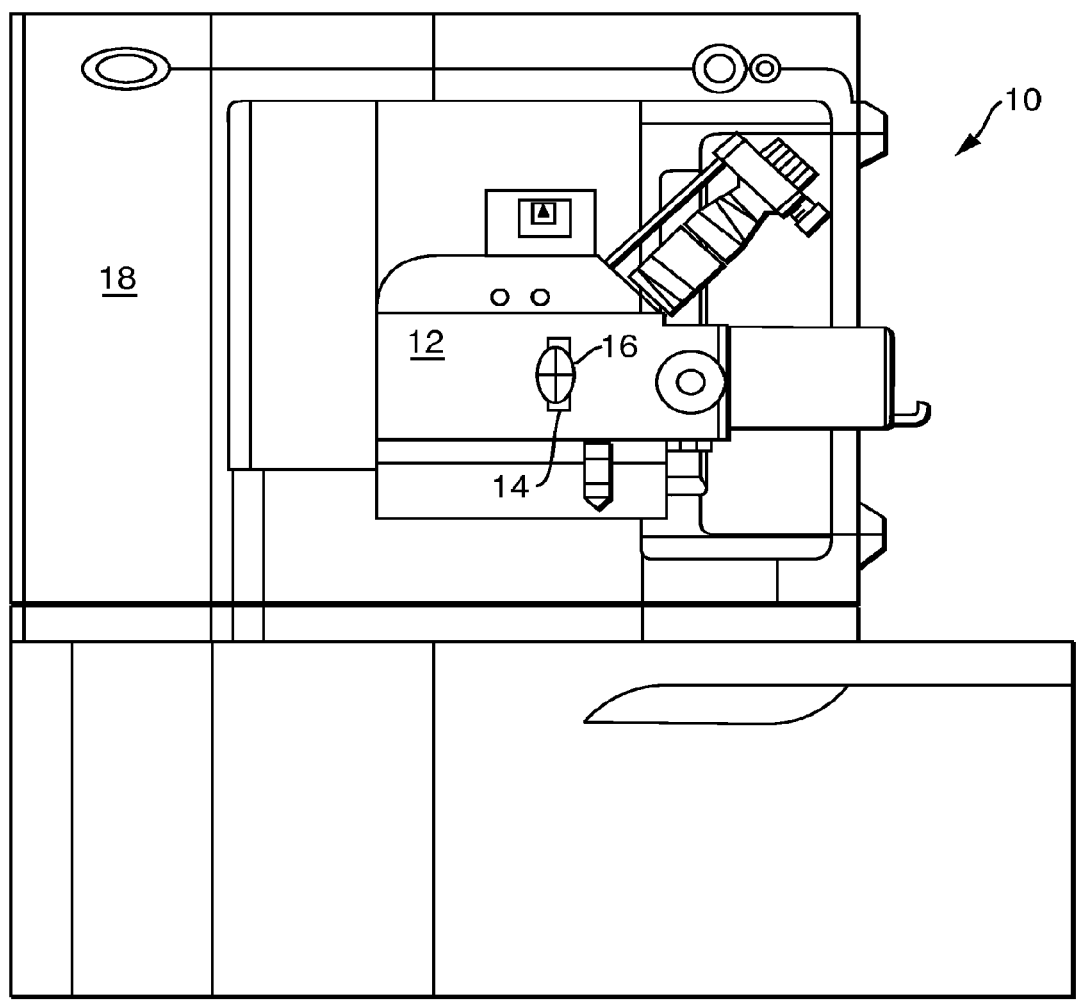
FIG. 1 is a front view of an embodiment of a liquid chromatography-mass spectrometer system including a liquid chromatography module with an installed microfluidic cartridge.

High-performance liquid chromatography (HPLC) instruments described herein have an installation chamber for receiving a microfluidic cartridge having an electrospray emitter, and for bringing the tip of the emitter into operable communication with mass spectroscopy components of the HPLC instrument. The microfluidic cartridge houses a substantially rigid, ceramic-based, multilayer microfluidic substrate (also referred to herein as a ceramic tile), for example, as described in US Patent Publication No. 2009/032135, Gerhardt et al., which is incorporated herein by reference. For protein samples, the ceramic is preferably a High-Temperature Co-fired Ceramic (HTCC), which provides suitably low levels of loss of sample due to attachment of sample to walls of conduits in the substrate. Formed in the layers of the substrate is a channel that operates as a separation column. Apertures in the side of the substrate provide openings into the channel through which fluid may be introduced into the column. Fluid passes through the apertures under high pressure and flows toward the electrospray emitter coupled at the egress end of the channel. Holes in the side of the microfluidic cartridge provide fluidic inlet ports for delivering fluid to the substrate. Each fluidic inlet port aligns with and encircles one of the fluidic apertures.

A clamping mechanism applies a mechanical force to one side of the microfluidic cartridge, urging the substrate against fluidic nozzles coupled to the installation chamber. The nozzles deliver fluid to the substrate through the fluidic inlet ports of the cartridge. Various embodiments of HPLC instruments arise, in part, from a realization that the various components, such as ports and nozzles, formed at least in part from a deformable material—at least partially elastically deformable material—such as a polymer, in combination with a mechanical force of sufficient strength, can be applied to a substantially rigid substrate to produce a tight, non-leaking seal between each nozzle and the surface of the substrate encircling an aperture. Preferably, the applied pressure, at the contact surface between the substrate and a tube, is greater than the pressure of a fluid passing through the tube into the substrate. A suitable polymer is, for example, polyether-ether-ketone, such as PEEK™ polymer (available from Victrex PLC, Lancashire, United Kingdom.) Preferably, an elastic modulus of the deformable material is lower than an elastic modulus of a surface material of the microfluidic substrate, to assist in repeatedly forming a fluid-tight seal.

Because a ceramic-based substrate may be prone to fracture if subjected to a mechanical force focused at a single small point and/or applied in a manner that tends to introduce shear stress (such as by tending to bend and/or twist the substrate,) the clamping mechanism preferably employs a multi-surfaced probe and/or preferably counters a force applied to (and perpendicular to) one side of the substrate with an equal, substantially collinear force applied to the opposite side of the substrate, in a manner to introduce compressive stress substantially without shear stress. A multi-surfaced probe, for example, presses against the substrate at multiple points of contact simultaneously. Thus, a probe is preferably configured to contact the substrate in a manner that tends to distribute forces and reduce or eliminate the potential for shear stress. Preferably, multiple contact sites associated with a probe are aligned with features that contact the opposite side of the substrate, to thus mitigate or eliminate introduction of shear stress by the clamping mechanism. Any or all of the features that contact the substrate, from either side, optionally include conduits, for gases and/or liquids, and optionally include electrical conductors, and/or optical conductors, and/or other communication pathways. The multiple points of simultaneous contact distribute the mechanical force over a greater area than that of a single point of contact. Preferably, the points of contact are associated with substantially equidistant points on a circle, and/or define a circular area of force distribution. Preferably, a component that contacts a substrate at multiple points receives an applied force at a single site, thus potentially reducing the likelihood or degree of twisting forces applied to a substrate. Further, the substrate preferably has some freedom of movement within the microfluidic cartridge, being free to float until the clamping mechanism is engaged, thus permitting the substrate to "self-adjust" its position during the clamping process so that stresses, other than compressive, do not impinge upon the substrate, and a housing portion of the cartridge does not apply substantial, if any, force to the substrate.

In addition to the substrate, the microfluidic cartridge houses internal circuitry and a temperature control unit for heating and cooling the substrate. An aperture in the microfluidic cartridge provides a window through which pogo pins supply low voltage and other electrical signals to internal circuitry. Another aperture in the microfluidic cartridge, near the tip of the electrospray emitter, operates as a gas inlet port that couples to a gas nozzle. Still another aperture, disposed near the emitter tip, serves as a high-voltage input port. A high-voltage cable couples to this high-voltage input port to deliver high voltage to the tip region of the emitter.

The mechanical force used to urge the tubing against the substrate also operates to establish connections between the high-voltage cable and the high-voltage input port, between the electrically conductive pogo pins and an electrical connector, and between the gas nozzle and the gas inlet port. Thus, a single act of clamping the microfluidic cartridge within the installation chamber concurrently establishes the various fluidic and electrical connections needed for operating the separation column.

FIG. 1 shows a front view of one embodiment of a liquid chromatography-mass spectroscopy (LC-MS) system 10 in which the invention may be embodied. The LC-MS system 10 includes a liquid chromatography module 12 having a slot 14 within which resides a fully installed microfluidic cartridge 16. As shown, the handle of the microfluidic cartridge 16 projects from the slot 14. The liquid chromatography module 12 is coupled to a mass spectroscopy (MS) unit 18. In one embodiment, the LC-MS system 10 is a modified version of a nanoACQUITY HPLC® system produced by Waters Corporation of Milford, Mass.

Figure 2:
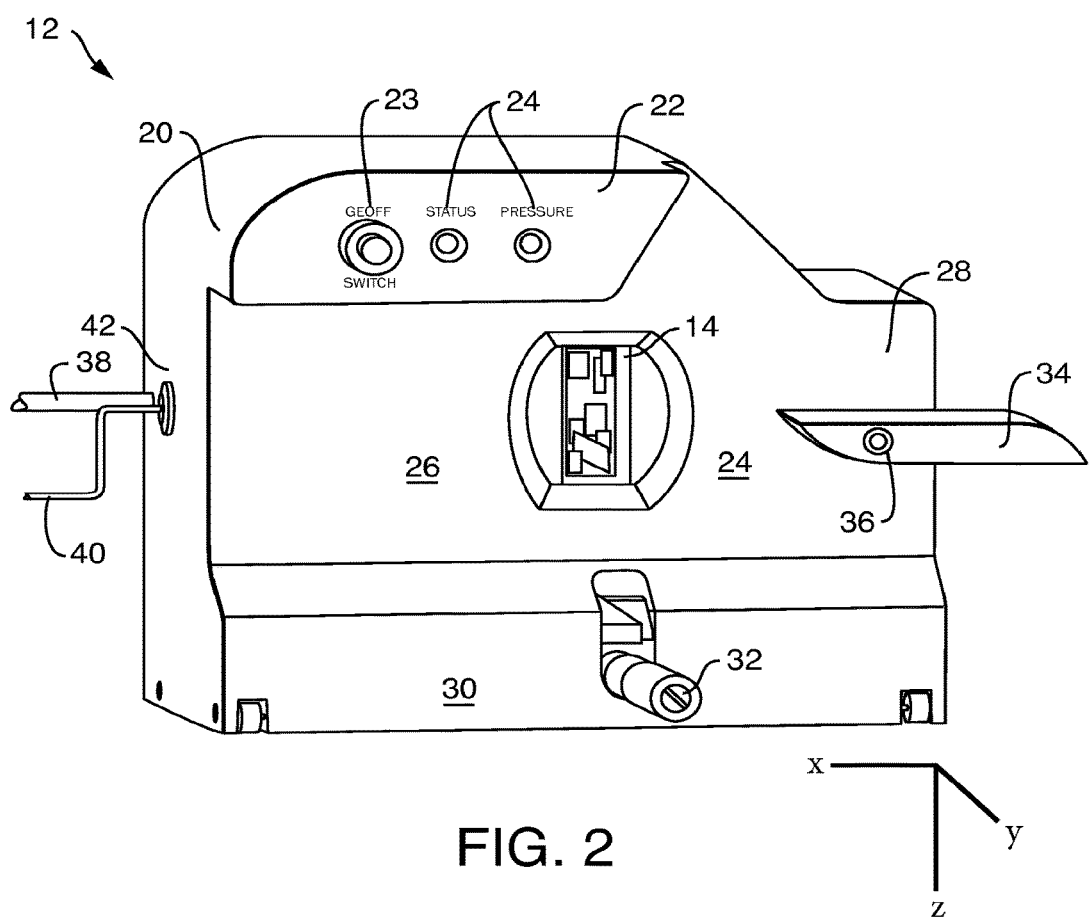
FIG. 2 is a front view of an embodiment of the liquid chromatography module.

FIG. 2 shows a front view of an embodiment of the liquid chromatography module 12 having a housing 20. The housing 20 has an upper section 22 with an on-off switch 23 and with status and pressure indicators 24, a middle section 26 having the slot 14 for receiving the microfluidic cartridge and an arm portion 28, and a lower section 30 having an adjustment knob 32 extending from an opening in the housing. The adjustment knob 32 is coupled to an interior x-translation stage (partly visible) for moving the microfluidic cartridge 16 along the x-axis. Adjustment knobs for y-translation and z-translation stages (not shown) also enable y-axis and z-axis adjustments of the position of the microfluidic cartridge relative to the MS unit 18 (FIG. 1). Such adjustments provide, for example, positioning of an emitter tip outlet in relation to an MS inlet orifice.

Coupled to the arm portion 28 is a lever 34 that is rotatable about a pivot point 36 between a clamped position and an unclamped position. In FIG. 2, the lever is in the unclamped position. Counterclockwise rotation of the lever about the pivot point, approximately 180 degrees, moves the lever into the clamped position. At one end of the housing, an electrical cable 38 and an electrical signal conductor 40 enter the housing through an opening 42 in the front of the housing. The electrical cable 38 supplies a high voltage, and the electrical signal conductor 40 supplies a low voltage, to the microfluidic cartridge, as described herein. Not shown are the microfluidic tubing and a gas line, which also enter the housing through the opening 42, for bringing fluid and gas, respectively, to the microfluidic cartridge.

Figure 3:
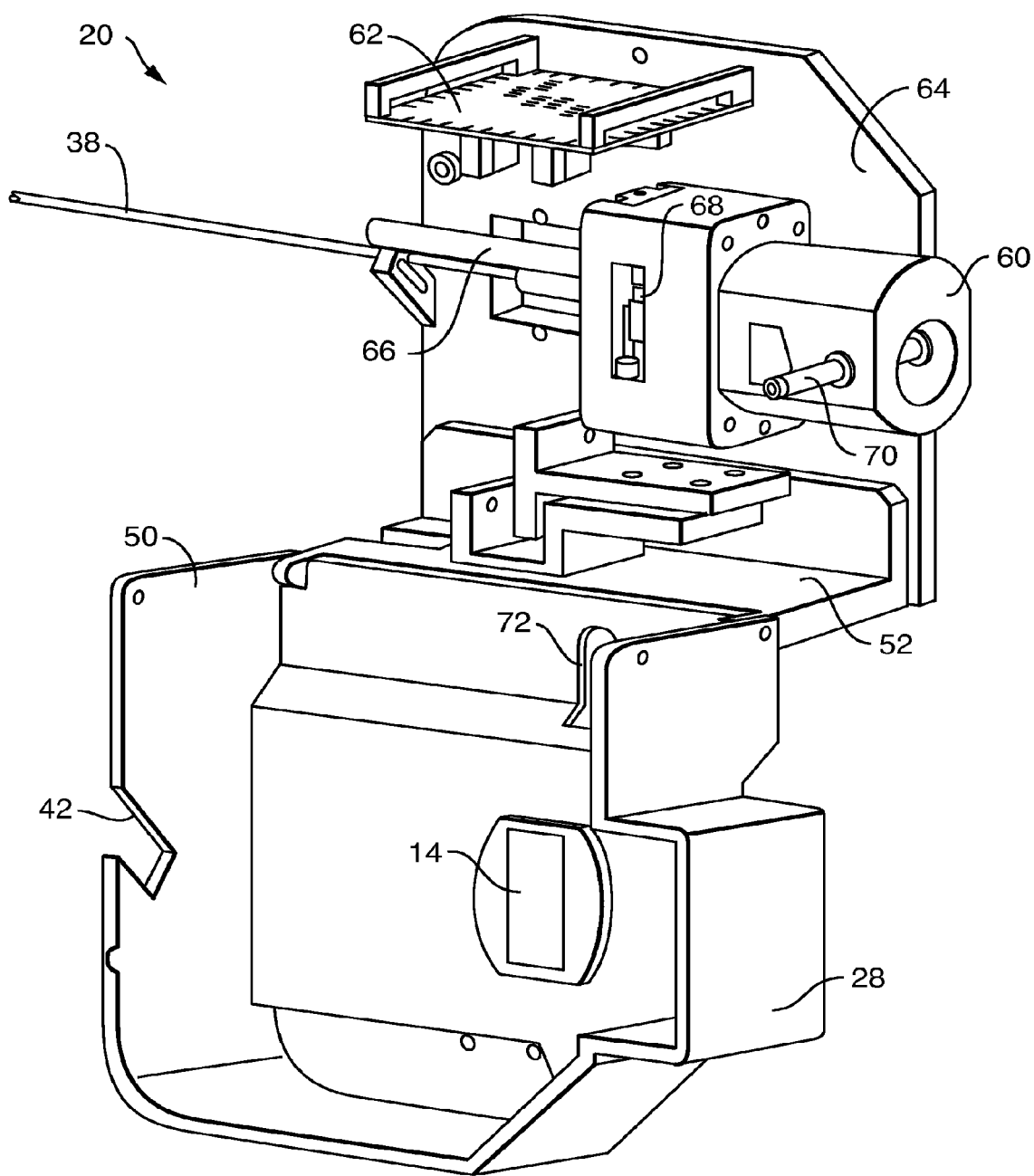
FIG. 3 is a view of the liquid chromatography module with an open cover to show a clamping assembly housed within.

FIG. 3 shows the housing 20 with its front cover 50 opened to expose a clamping assembly 60 within. A hinge along a base edge of the housing attaches the front cover 50 to a translation stage support 52. The translation stages and adjustment knobs are absent from the drawing to simplify the illustration. Other components residing within the housing include a circuit board 62. The translation stage support 52, clamping assembly 60, and circuit board 62 are coupled to a rear panel 64 of the housing.

The electrical cable 38 and an electrical conduit 66 couple to one side of the clamping assembly 60. The electrical cable carries a high voltage (e.g., 3000 volts), and the electrical conduit 66 bundles a plurality of low-voltage electrical conductors. Not shown are the microfluidic tubing and gas line that are also coupled to the same side of the clamping assembly 60 as the electrical cable 38 and electrical conduit 66.

The clamping assembly 60 has a slot 68 for receiving a microfluidic cartridge and a post 70 to which the lever 34 (FIG. 2) is attached. When the front cover 50 is closed, the slot 14 in the front cover 50 aligns with the slot 68 of the clamping assembly 60, the adjustment knob 32 of FIG. 2 (not shown in FIG. 3) projects through the opening 72 in the front cover 50, and the post 70 projects through another opening, which is obscured by the sidewall of the arm portion 28.

Figure 4:
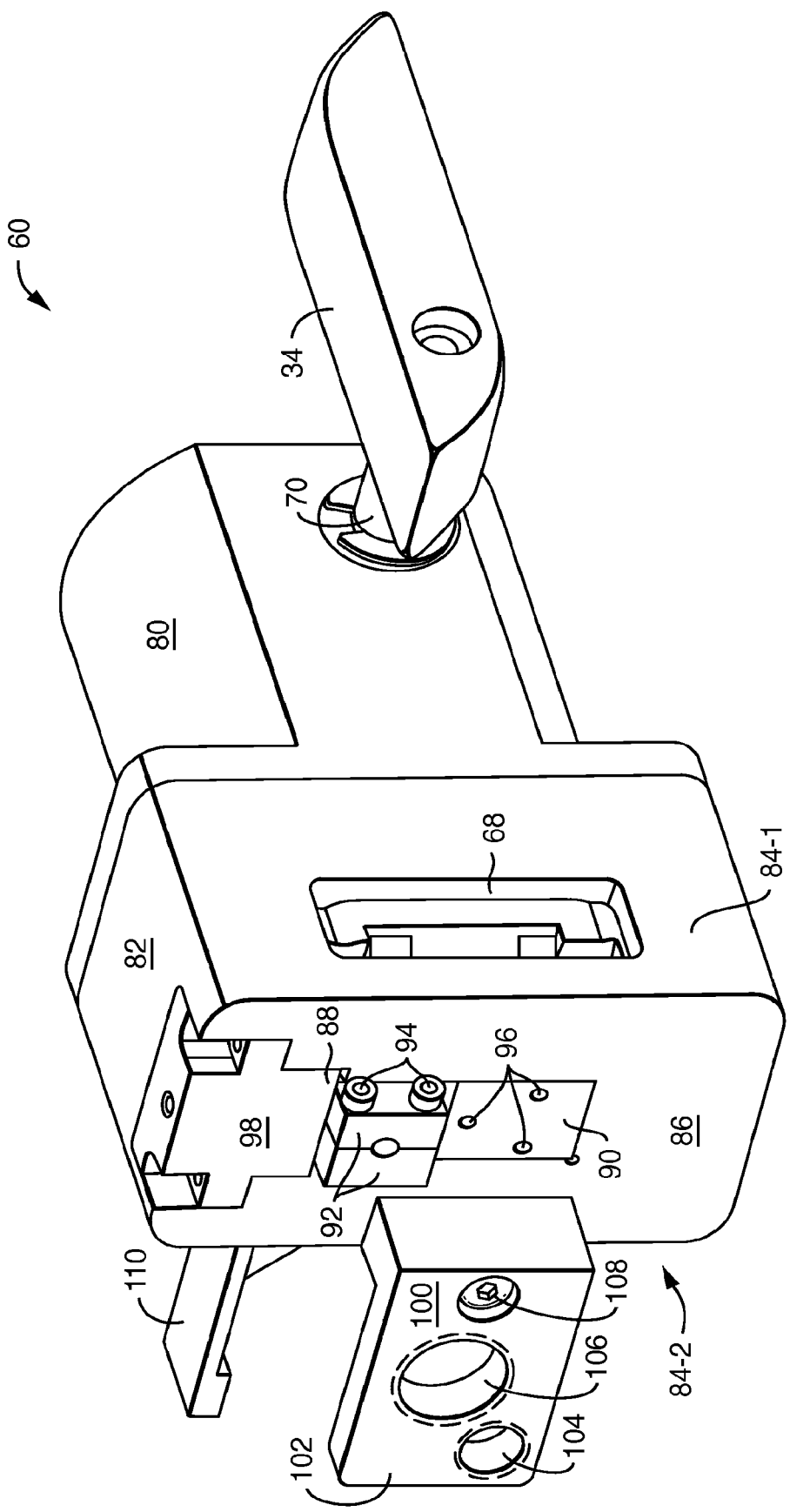
FIG. 4 is an isometric view of an embodiment of the clamping assembly housed within the liquid chromatography module.

FIG. 4 shows an embodiment of the clamping assembly 60 having a body 80 coupled to an end housing 82. The post 70 joins the lever 34 to one side (called herein the front side) of the body 80. The end housing 82 has opposing sidewalls 84-1, 84-2 (generally, 84) spatially separated by a back wall 86. The sidewall 84-2 is not visible; the reference numeral points generally to the area of the side wall 84-2. Sidewall 84-1 has the slot 68 (FIG. 3) that is adapted to receive the microfluidic cartridge 16 (FIG. 1). Sidewall 84-2 has a corresponding slot (not shown) aligned with the slot 68 in the sidewall 84-1 such that the microfluidic cartridge 16 passes through both slots upon being installed into the clamping assembly 60.

The back wall 86 of the end housing 82 has a pogo pin block 88 and a fluidic block 90. The pogo pin block 88 includes a two-piece bracket 92, joined by fasteners 94, for retaining the electrical conduit 66 (not shown) therebetween. The pogo pin block 88, mostly obscured in FIG. 4 by the two-piece bracket 92, is disposed adjacent to and above the fluidic block 90. This embodiment of fluidic block 90 has three apertures 96 for receiving the ends of tubes that deliver fluid. A spacer block 98 secures the pogo pin block 88 and fluidic block 90 within a slot (shown in FIG. 8) in the back wall.

Projecting from a surface of the back wall 86 is an L-shaped retainer 100 having a major surface 102 with three openings 104, 106, 108 therein. The opening 104 is for retaining a gas line (not shown) that is coupled to the clamping assembly 60; the opening 106 is for retaining the high-voltage electrical cable 38 (FIG. 3), and the opening 108 is for receiving a fastener that joins the retainer 100 to the back wall 86. Extending from the rear side of the clamping assembly 60 (i.e., the side presented to the MS unit 18 of FIG. 1) is an arm 110 used to restrict the extent to which the microfluidic cartridge 16 can be inserted through the slots 68.

Figure 5:
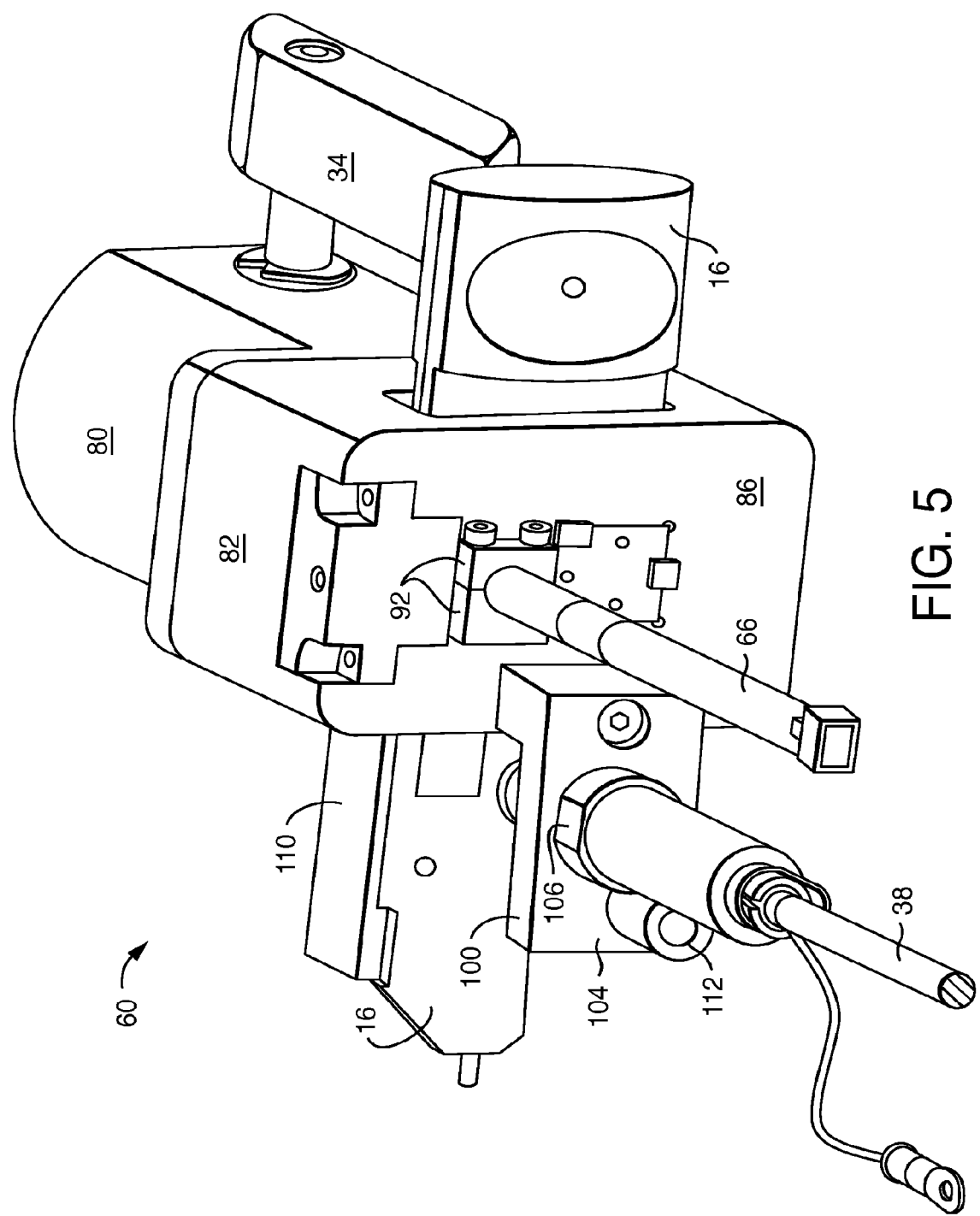
FIG. 5 is a side view of the clamping assembly.

FIG. 5 shows a side view of the clamping assembly 60, with the microfluidic cartridge 16 passing through both slots in the sidewalls 84 of the clamping assembly 60. The arm 110 catches a nook in an upper edge of the microfluidic cartridge 16, preventing the microfluidic cartridge from sliding further through the slots 68. The high-voltage electrical cable 38 couples to the opening 106 and the electrical conduit 66 couples to the two-piece bracket 92 of the pogo-pin block. In addition, a coupler 112 connects to the opening 104 in the L-shaped retainer 100.

Figure 6:
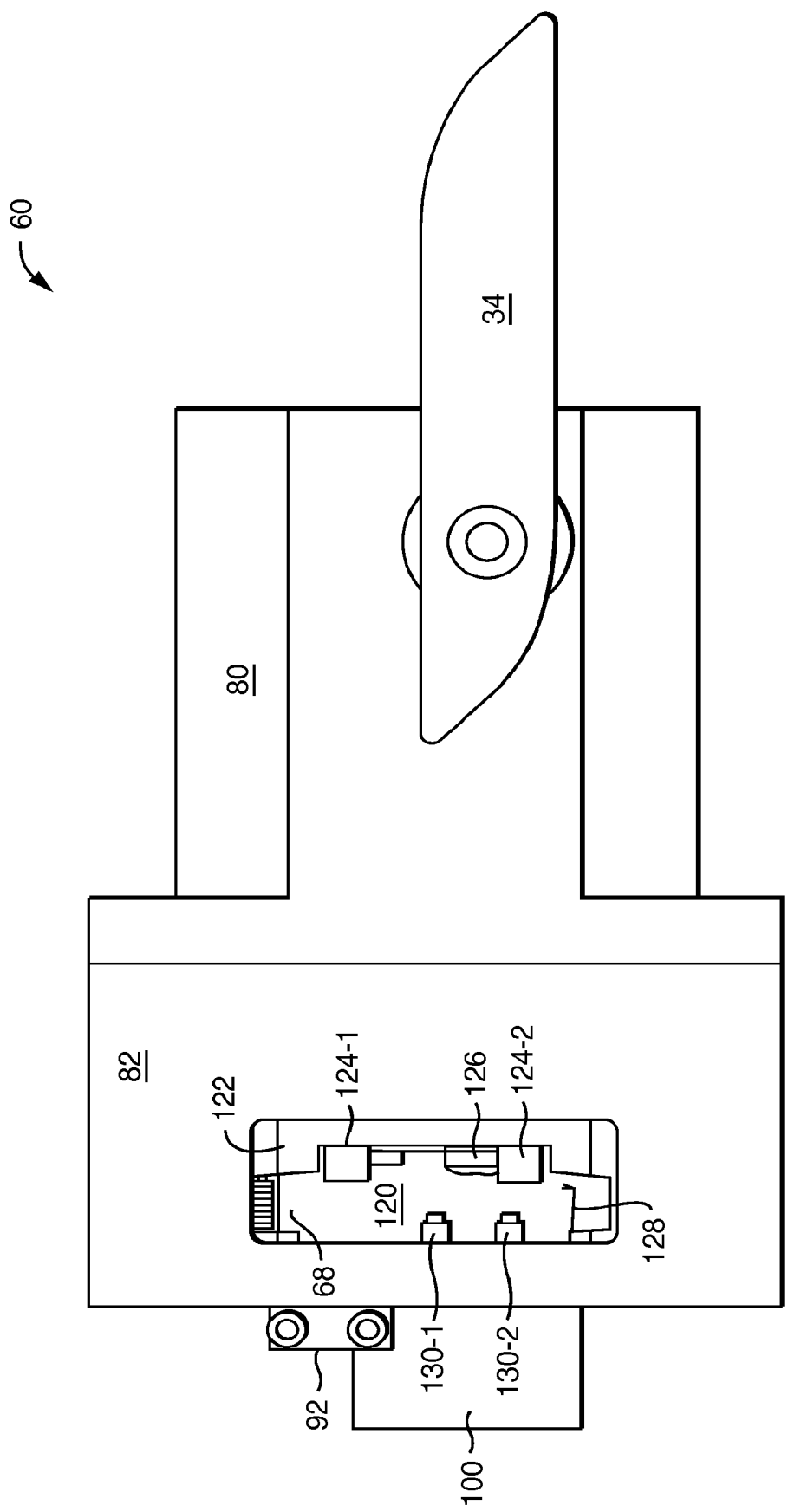
FIG. 6 is a front view of the clamping assembly.

FIG. 6 shows a front view of the clamping assembly 60 and a chamber 120 visible through the slots 68. Within the chamber 120 is a carriage 122 for receiving the microfluidic cartridge 16. Extending inwardly into the chamber 120 from one side (i.e., in FIG. 6, the right side) of the carriage 122 are upper and lower springs 124-1, 124-2, respectively, and the tip of a plunger 126. Extending inwardly into the chamber 120 from the opposite side (i.e., from the direction of the back wall 86 of the end housing 82) is a guide pin 128 and a plurality of microfluidic nozzle tips 130-1, 130-2. In this embodiment, the microfluidic nozzle tip 130-2 obscures a third microfluidic nozzle tip 130-3 (FIG. 7), which is horizontally in line with the microfluidic nozzle tip 130-2.

Figure 7:
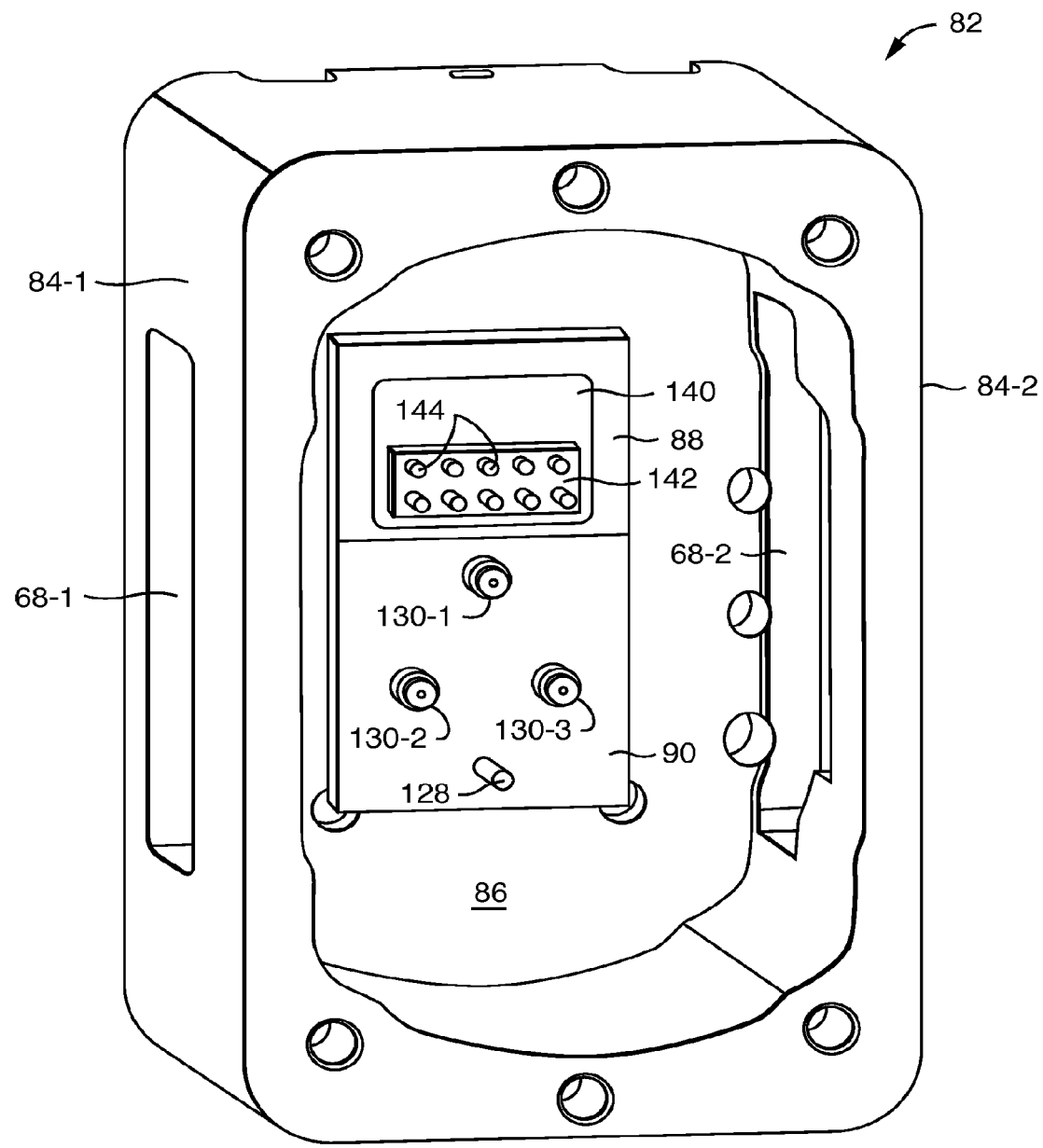
FIG. 7 is a view of an embodiment of an end housing of the clamping assembly.

FIG. 7 shows an interior view of one embodiment of the end housing 82, including the opposing sidewalls 84-1, 84-2, separated by the back wall 86. The sidewall 84-1 has the slot 68-1, and the sidewall 84-2 has the slot 68-2. Installed in the back wall 86 are the pogo pin block 88 and fluidic block 90.

The interior side of the pogo pin block 88 has a recessed region 140 with a pogo pin electrical connector 142 projecting inwardly from a surface thereof. In this example, the electrical connector 142 has ten electrically conductive pogo pins 144 for conducting electrical signals. Each pogo pin 144 is an individual cylindrical, spring-loaded electrical conductor for transmitting electrical signals.

The interior side of the fluidic block 90 has the plurality of microfluidic nozzles 130-1, 130-2, 130-3 (generally, 130) of FIG. 6 projecting therefrom. In one embodiment, the nozzles 130 are three in number and arranged in a triangular pattern. The locations of these nozzles 130 are fixed with respect to each other. Fluid delivered by microfluidic tubes to the apertures 96 (FIG. 4) on the exterior side of the fluidic block 90 exits through these nozzles 130. Situated below the triangular pattern of nozzles 130, aligned with the nozzle at the apex of the triangle, is the guide pin 128.

Figure 8:
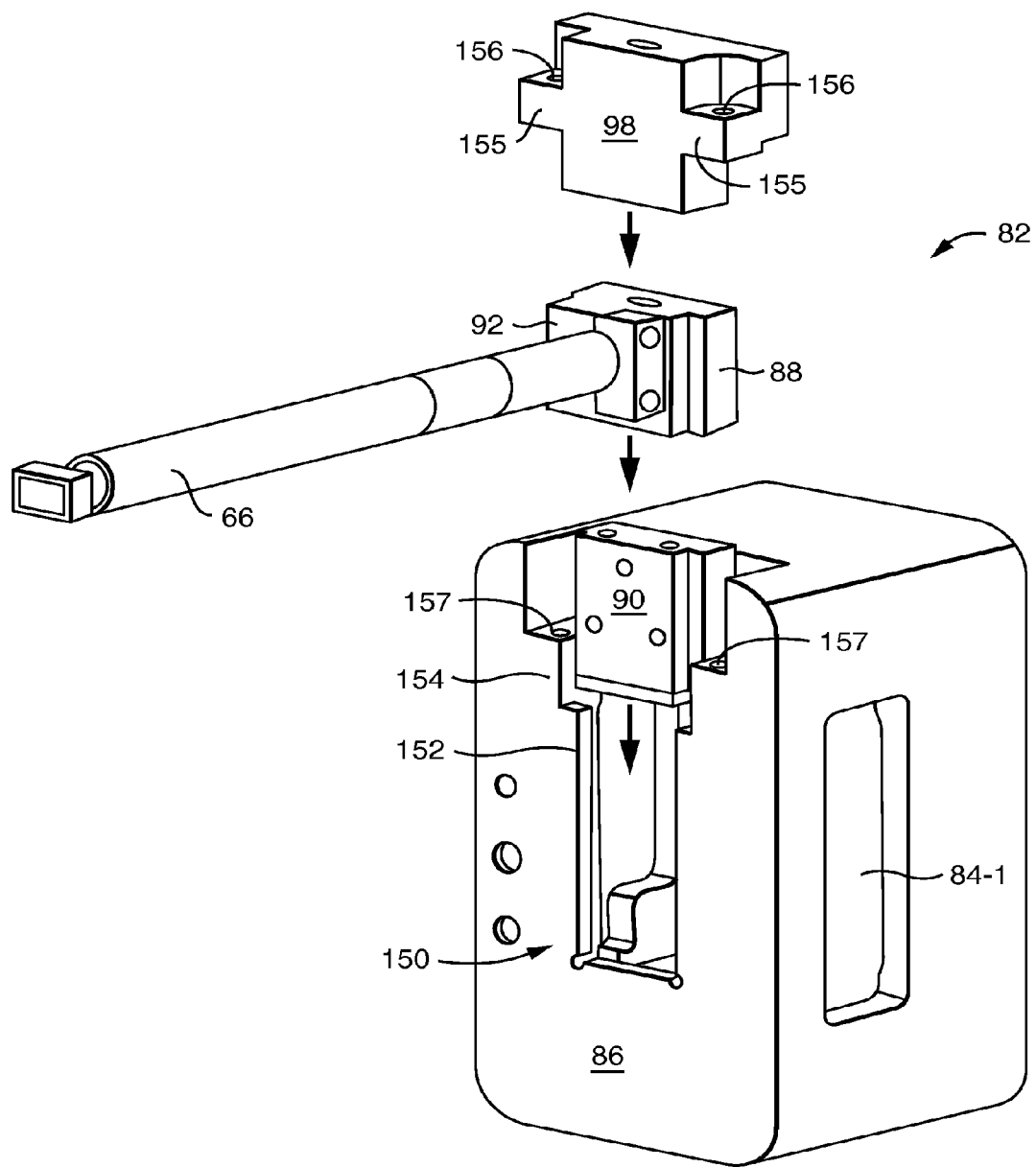
FIG. 8 is an exploded isometric view of the end housing.

FIG. 8 shows an exploded view of the end housing 82, to illustrate an assembly process of the back wall 86. The back wall 86 has a slot 150 into which slide, in succession, the fluidic block 90, pogo pin block 88, and spacer 98. The slot 150 has a lower rectangular region 152 and a tiered upper region 154. The lower region 152 is adapted to receive the fluidic block 90 and pogo pin block 88. The shape of the upper region 154 is adapted to receive the spacer 98. The spacer 98 has shoulders 155 with holes 156 therein, through which fasteners can join the spacer to respective holes 157 in the back wall 86, thus securing the blocks 88, 90, 98 within the slot 150.

Figure 9:
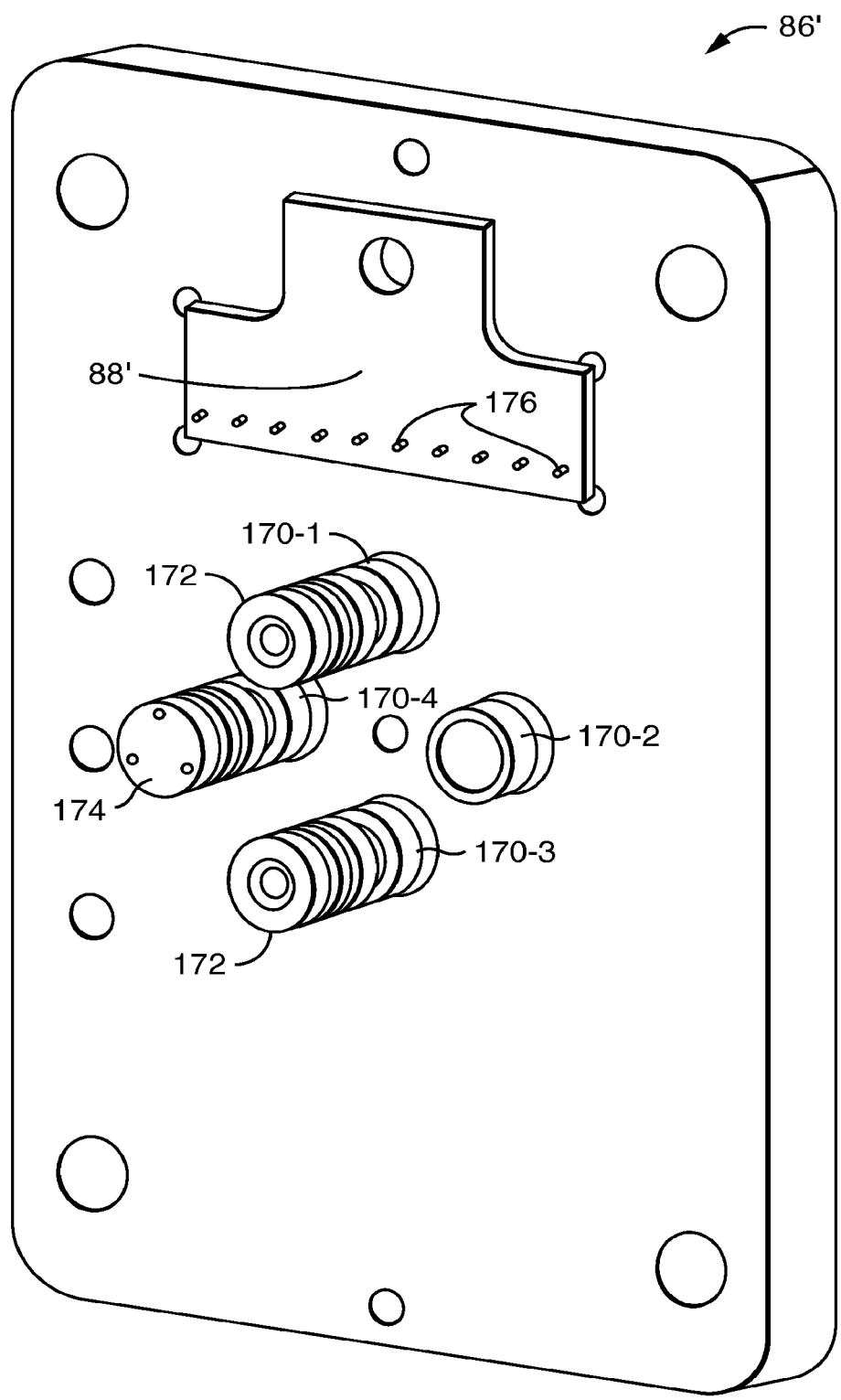
FIG. 9 is an exterior view of an alternative embodiment of a back wall for the end housing.
Figure 10:
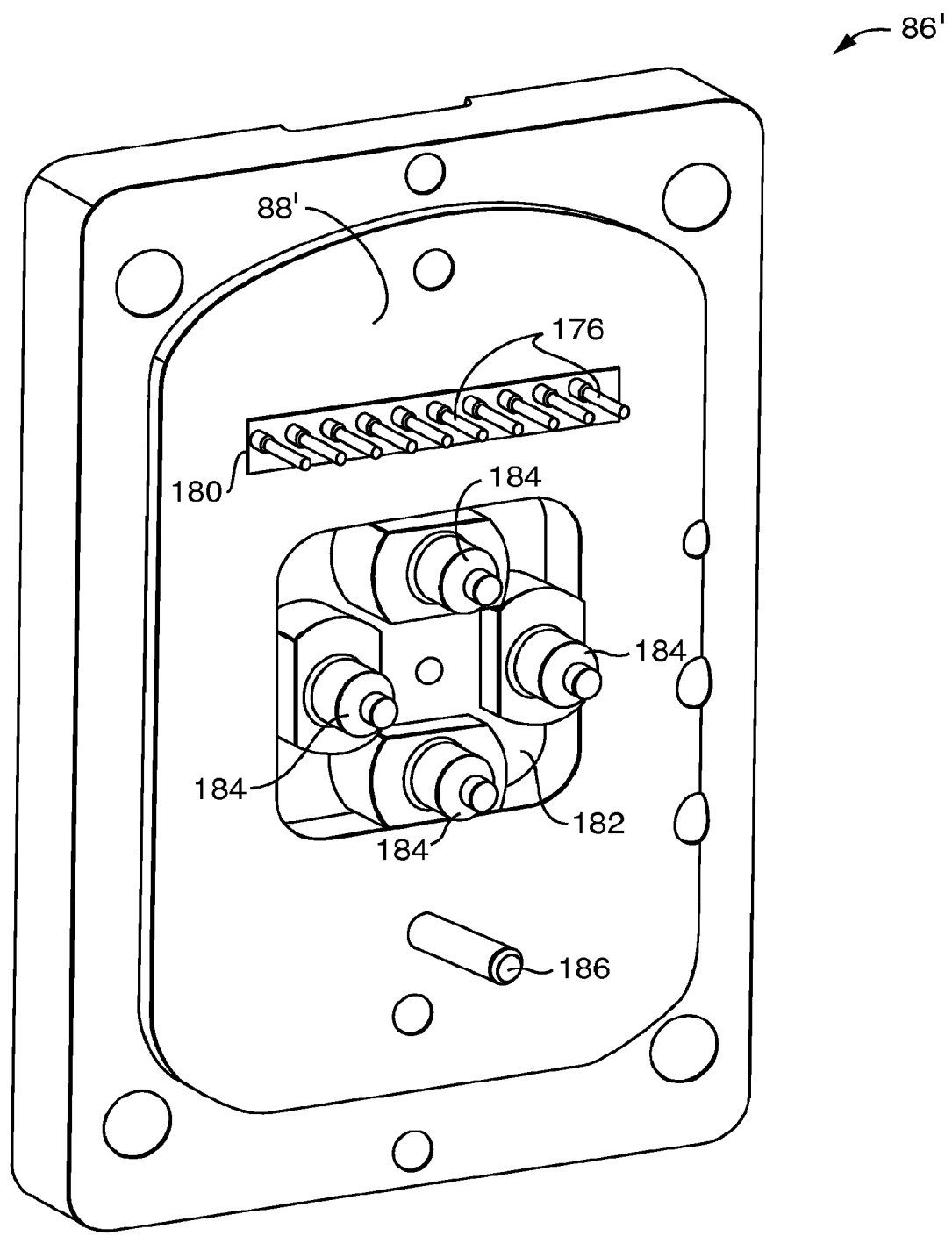
FIG. 10 is an interior view of the alternative embodiment of a back wall for the end housing.

FIG. 9 and FIG. 10 show an alternative embodiment of a back wall 86' for the end housing 82; FIG. 9 shows an exterior side of the back wall 86', and FIG. 10 shows an interior side. In this embodiment, the back wall 86' has four nozzles to contact a microfluidic substrate rather than the three nozzles 130 of the fluidic block 190 described in FIG. 7. The back wall 86' includes four fluidic inlet ports 170-1, 170-2, 170-3, 170-4 (generally, 170) arranged in a diamond pattern. Each fluidic inlet port 170 includes a round fitting (most visible in port 170-2 of the four ports) that projects generally orthogonal from the back wall 86'. Each fluidic inlet port 170 is floating with respect to the other ports 170; that is, the fluidic inlet ports 170 themselves are not fixed to the back wall 86' so that each fluidic inlet port 170 can move slightly and independently of the other ports 170.

As examples of fluidic plumbing, the tip of a microfluidic tube 172 is press fit into fluidic inlet ports 170-1 and 170-3, whereas fluidic inlet port 170-4 is blocked with a plug 174 (i.e., unused), and fluidic inlet port 170-2 is open. The back wall 86' also includes an alternative embodiment of a pogo pin block 88' having a single row of electrical connectors 176 (here, e.g., ten in number).

FIG. 10 shows an interior side of the alternative embodiment of the back wall 86' described in FIG. 9. The interior side of the pogo pin block 88' has a recessed region 180 from which project the row of electrically conductive pogo pins 176. Below the row of pogo pins is a second recessed region 182. Projecting from this recessed region 182 are four microfluidic nozzles 184, each corresponding to one of the ports 170 on the exterior side of the back wall 86'. Fluid delivered by microfluidic tubes 172 to the ports 170 on the exterior side of the back wall 86' exits through these nozzles 184. Situated below the diamond pattern of nozzles 184 is an alignment pin 186, similar in function to the guide pin 128.

Figure 11:
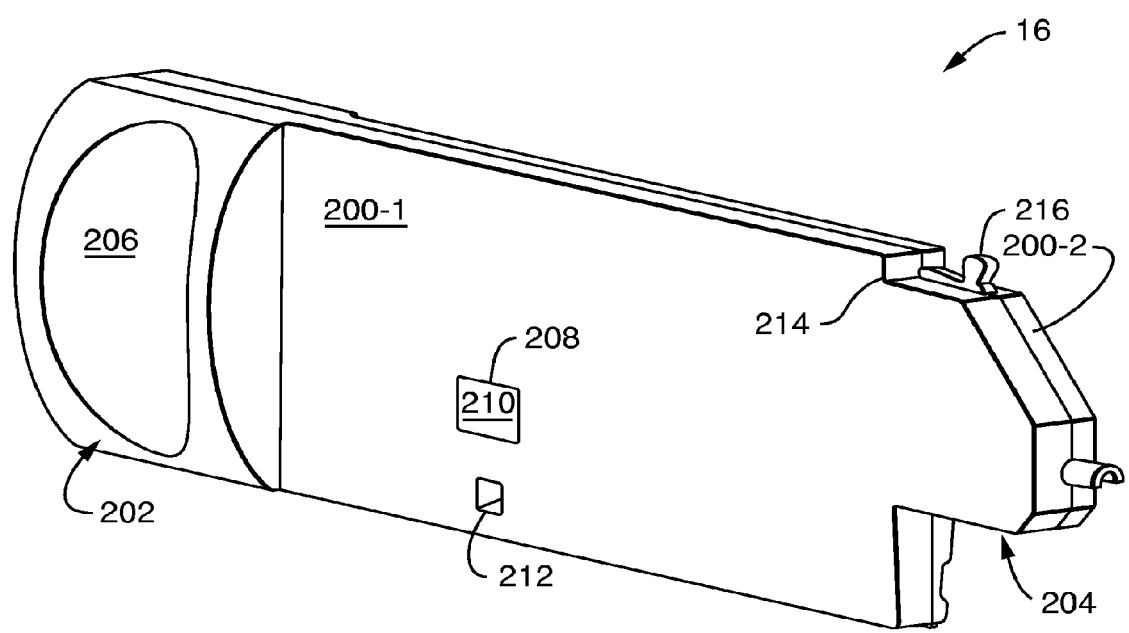
FIG. 11 is a view of the right side of one embodiment of a microfluidic cartridge.

FIG. 11 shows a right side view an embodiment of the microfluidic cartridge 16 that works in conjunction with the type of nozzle arrangement described in FIG. 7. As described further below, the microfluidic cartridge 16 houses an emitter, a microfluidic substrate, a heater, and circuitry, and operates as an electromechanical interface for the delivery of voltages, electrical signals, and fluids (gas and liquid) to the various components housed within the microfluidic cartridge 16.

This embodiment of microfluidic cartridge 16 is made by joining two casing sections 200-1, 200-2, for example, by snapping the halves together, or using glue or mechanical fasteners, or any combination thereof. The two casing sections are also referred to herein as the left and right sides of the microfluidic cartridge 16, with the terms left and right being determined by the orientation of the microfluidic cartridge 16 when it is inserted into the clamping assembly 60. It is to be understood that such terms as left, right, top, bottom, front, and rear are for purposes of simplifying the description of the microfluidic cartridge, and not to impose any limitation on the structure of the microfluidic cartridge itself.

The right casing section 200-1 has a grip end 202 and an emitter end 204. A curved region 206 within the grip end 202 provides a finger hold by which a user can grasp the microfluidic cartridge 16 when inserting and removing it from the liquid chromatography module 12.

In the side of the casing section 200-1 is a rectangular-shaped window 208, within which resides a push block 210. The surface of the push block 210 lies flush with the surface of the right casing section 200-1. As described further below, the push block 210 is not rigidly affixed to the right casing section 200-1, and can move slightly in, out, up, down, left, or right; that is, the push block 210 floats within the window 208. In one embodiment, the push block 210 is made of metal. Thus, a suitable push block, in some various embodiments of the invention has self-leveling features, and is included in a cartridge or elsewhere in a clamping mechanism. The expression "floats freely", and the like, is used herein to mean, as will be apparent in context, having a mechanical degree of freedom that permits self alignment; self alignment preferably refers to an ability to tilt relative to a plane defined by a neighboring component, to mate with the neighboring component without introduction of significant bending stress.

Disposed below the push block 210 is an opening 212, which extends completely through both casing sections 200-1, 200-2. Hereafter, the opening 212 is referred to as a through-hole 212. At the emitter end 204 is a nook 214 in the top edge of the microfluidic cartridge 16. Within the nook 214, a movable fin 216 projects through the top edge between the casing sections 200-1, 200-2.

Figure 12:
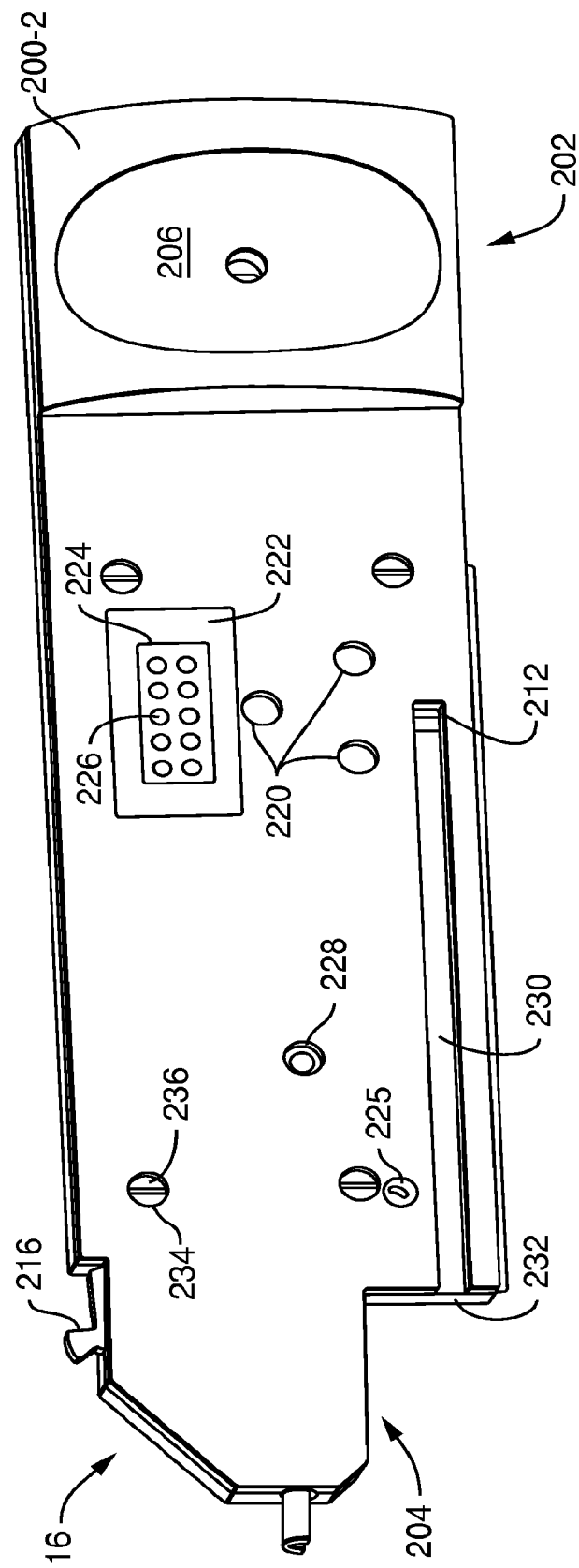
FIG. 12 is a view of the left side of the microfluidic cartridge.

FIG. 12 shows the left casing section 200-2 of the microfluidic cartridge 16. Like the right casing section 200-1, the left casing section 200-2 has a grip end 202 with a curved region 206 and an emitter end 204. Approximately central in the length of the left casing section 200-2 are three nozzle openings 220 in a triangular pattern that matches the triangular arrangement of the nozzles 130 of the fluidic block 90 (FIG. 7). The triangular pattern is desirable, to define a circular load pattern. The center of the circle is preferably aligned to the axis of motion of a plunger 126 (FIG. 20) of the clamping assembly 60 (FIG. 6) to provide a load balance on the metal-plate bosses 260 of the push block 210. A third fluidic port is used, for example, for a calibration port; an operator can run a calibration fluid. The other two ports provide access to, for example, the analytical column and the trap column.

Concentrically located behind each nozzle opening 220 is a microscopic fluidic aperture in the side of a microfluidic substrate housed within the microfluidic cartridge. The fluidic conduits of the microfluidic nozzles 130 of the fluidic block 90 have much larger inner diameters than the size of the microscopic apertures in the substrate, which facilitates alignment therebetween. In one embodiment, each microscopic fluidic aperture has a 0.003" square cross section, and each microfluidic nozzle 130 has a 0.013" orifice (lumen with a circular cross section) that aligns with and circumscribes the microscopic fluidic aperture on the substrate.

The microfluidic nozzles 130 utilize a polymer-to-ceramic interface, relying only on the compressive stress provided by the clamping assembly 60 (FIG. 6) to provide a fluidic seal; that is, the clamping assembly 60 provides a greater pressure at the polymer-to-ceramic interface than the operating fluidic pressure. For example, for an operating fluidic pressure of 15,000 psi, a clamping load of 130 pounds across the total surface area of the nozzle-to-substrate interface can produce an effective fluidic seal. Generally, the selected clamping load is preferably selected in cooperation with the interfacial surface area to provide an interfacial pressure greater than a selected operating pressure.

Directly above the apex of the triangularly arranged nozzle openings 220 is a rectangular depression 222 within the left casing section 200-2. The depressed region 222 surrounds a rectangular-shaped window 224 through which an array of electrical contacts 226 is accessed. The electrical contacts 226 are electrically conductive pads for making electrical contact with the pogo pins 144 of the pogo pin block 88 (FIG. 7). The array of electrical contacts 226 is part of a flex circuit overlaid upon the microfluidic substrate, as described further below in connection with FIG. 13.

At the emitter end 204, the left casing section 200-2 has a gas inlet port 225 for receiving a gas nozzle and a high-voltage input port 228 for receiving the tip (pogo-pin) of the high-voltage electrical cable 38 (FIG. 5). A plurality of holes 234 hold alignment pins 236 that are used to align the casing sections 200-1, 200-2 when the halves are being joined.

The left casing section 200-2 further includes a rectangular-shaped groove 230 along its bottom edge. The groove 230 has an open end 232 at the emitter end 204, extends laterally therefrom, and terminates at the through-hole 212 situated below the nozzle openings 220. In addition, the groove 230 receives the guide pin 128 (FIG. 7) when the microfluidic cartridge 16 is inserted into the slot 68 (FIG. 4) of the clamping assembly 60. When the guide pin 128 reaches the through-hole 212, then the microfluidic cartridge 16 is fully installed in the chamber 120 and in position for clamping.

Figure 13:
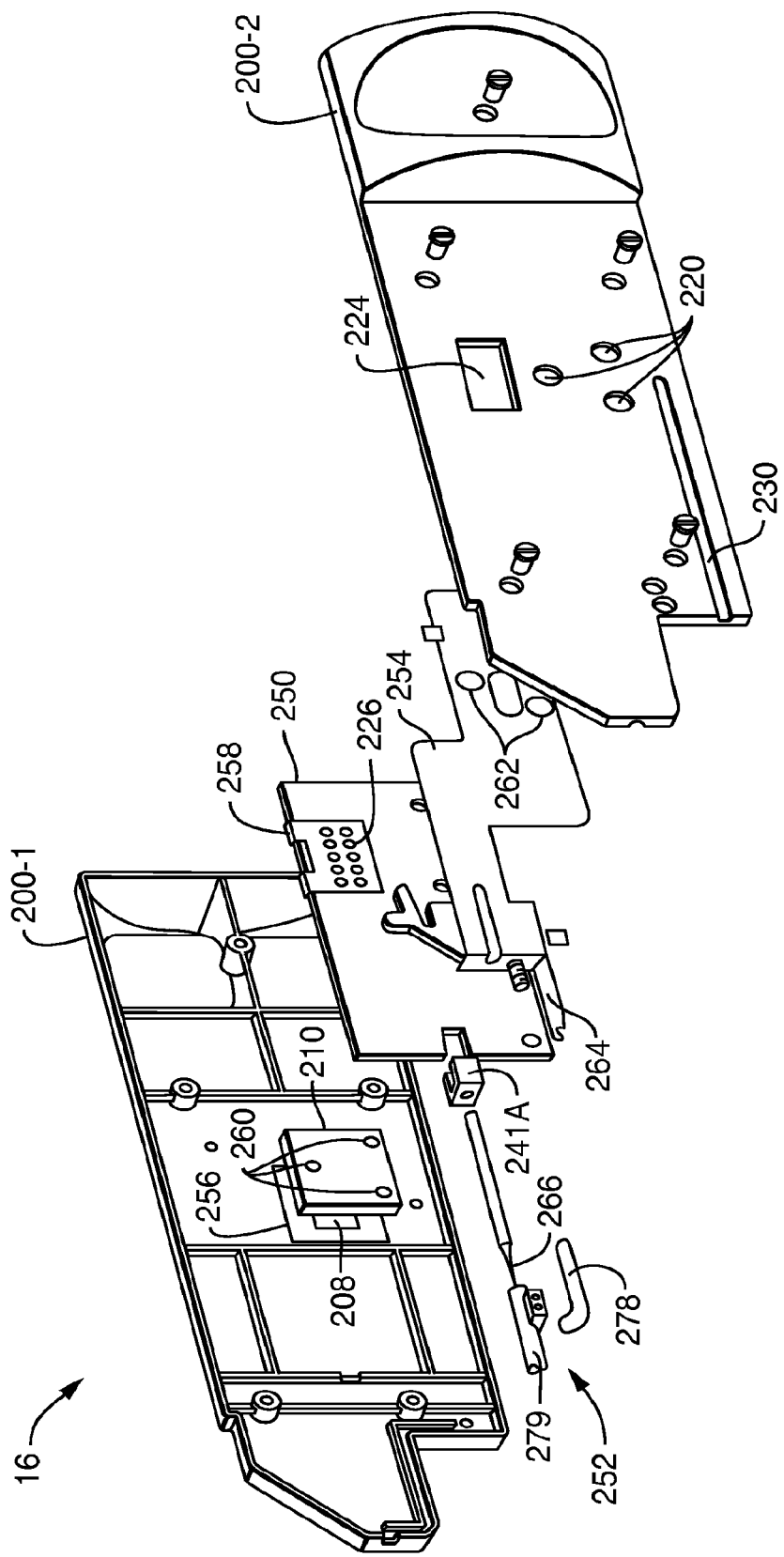
FIG. 13 is an exploded view of the microfluidic cartridge.

FIG. 13 shows an exploded view of the microfluidic cartridge 16, and the various components housed within. Disposed between the right casing section 200-1 and the left casing section 200-2 are a microfluidic substrate 250, an emitter assembly 252 (also referred to herein as a "spray unit") that couples to the microfluidic substrate, and a shutter 254. On the interior side of the right casing section 200-1 is a rectangular recess 256 adapted to closely receive the push block 210 (i.e., the push block 210 snaps into and floats within the recess 256). With the push block 210 sitting within this recess 256, a raised portion of the push block (on its opposite unseen side) enters the window 208 in the side of the right casing section 200-1.

In addition, this embodiment of push block 210 has three raised bosses 260, each with a planar face. The planar faces of the three bosses press simultaneously against the side of the microfluidic substrate when an urging force is applied to the push block 210 from an exterior side of the first casing section 200-1, spreading out the force to avoid a single concentrated point of contact. Each raised boss 260 aligns directly opposite one of fluidic apertures in the microfluidic substrate 250, and thereby applies pressure (when the push block is pushed) directly opposite one of the nozzle openings 220 in the left casing section 200-2, thus avoiding production of shear stresses by, for example, twisting and or bending the microfluidic substrate 250.

Other embodiments can have more, or fewer, than three bosses. In general, the number of bosses corresponds to the number of fluidic apertures (which may include dummy apertures) in the microfluidic substrate 250, so that there is one boss for each fluidic aperture, aligned directly opposite that fluidic aperture. In general, the number of bosses corresponds to the number of fluidic nozzles and dummy nozzles that contact the substrate 250, so that all bosses align with a corresponding nozzle. The number and arrangement of bosses and nozzles are optionally selected to control application of undesirable stresses to the microfluidic substrate 250.

The assembly 252 includes an emitter 266, an emitter retainer 241A that positions and/or aligns the emitter 266 with the substrate 250, and a sheath-gas component 279. The component 279 receives a sheath gas via a tube 278, which is disposed in the housing sections 200-1, 200-2. The retainer 241A aligns a lumen of the emitter 266 with an outlet port of the substrate 250. Preferably, additional component(s) urge the emitter 266 into contact with the substrate 205, with sufficient force to provide a greater interfacial pressure than a pressure of an eluent flowing through the outlet port into the lumen of the emitter 266.

Folded over a top edge of the microfluidic substrate 250, a flex-circuit assembly 258 includes the array of electrical contacts 226. As described in FIG. 12, these electrical contacts 226 are accessible through the window 224 in the left casing section 200-2. Further, the shutter 254 has holes 262 that align with the nozzle openings 220 in the side of the left casing section 200-2 so that the microscopic fluidic apertures in the surface of the microfluidic substrate 250 are exposed. In addition, the shutter 254 has the fin 216 (FIG. 11) and an emitter tube 264 that partially envelopes an electrospray emitter 266.

The substrate 250 is optionally formed in the following manner. Five green-sheet layers, for multiple substrates 250, are pressed together, after desired patterning. Vias for fluidic apertures are laser etched in one or both sides of the pressed sandwich. Edge portions are defined by laser etching. After firing, individual substrates 250 are snapped apart. Edges, or portions of edges, are optionally polished.

Figure 14:
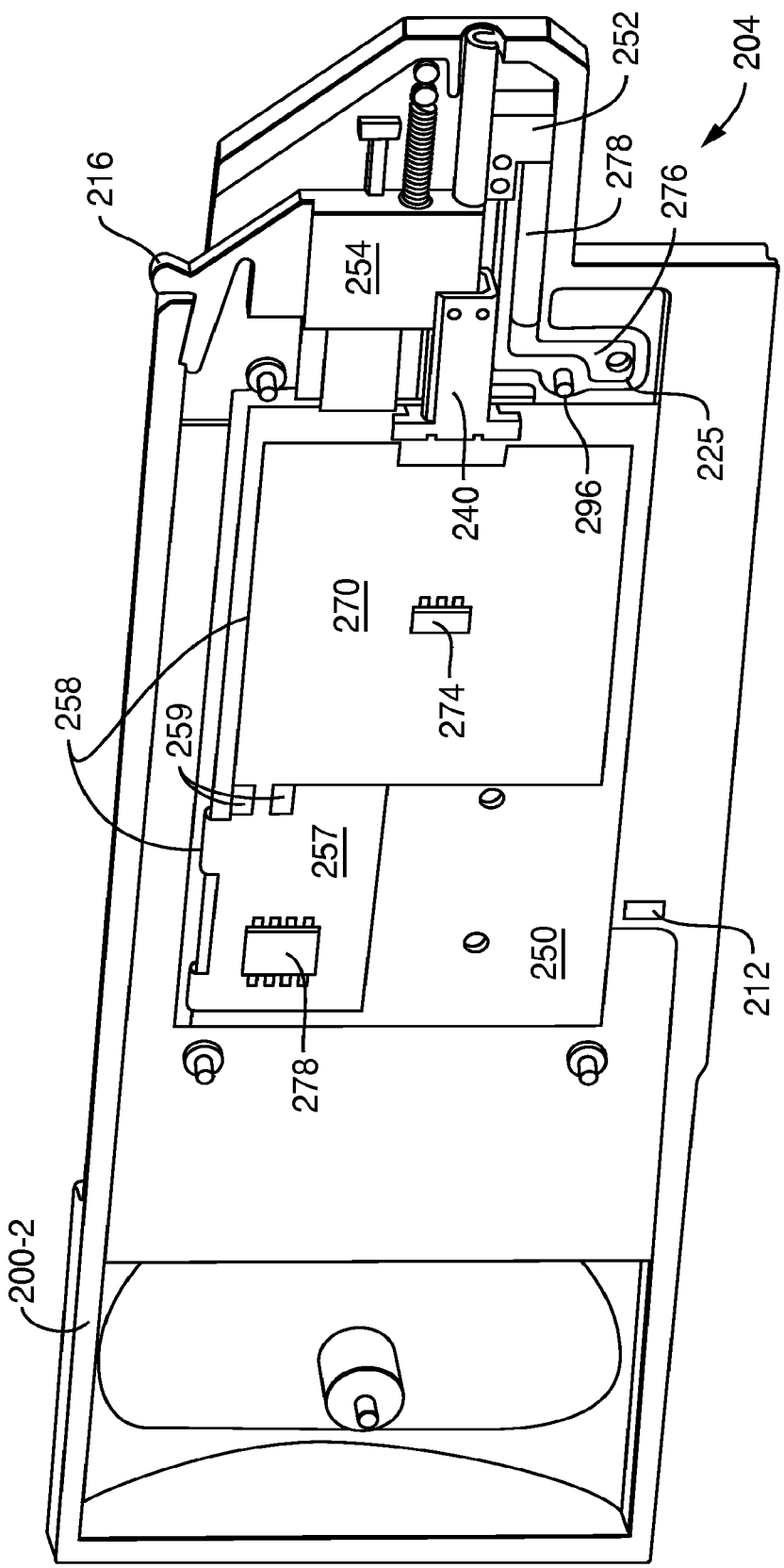
FIG. 14 is a side view of the microfluidic cartridge with the right side removed.

FIG. 14 shows a right side view of the microfluidic cartridge 16 with the right casing section removed to reveal various components housed within and to show various features of the interior side of the left casing section 200-2. The various components include the microfluidic substrate 250 and the shutter 254, both of which are coupled to the left casing section 200-2 as shown.

On the surface of the microfluidic substrate 250 is the flex-circuit assembly 258, comprised of a control circuitry portion 257 and a heater portion (hereafter, heater 270). The flex-circuit assembly 258 folds over a top edge of the microfluidic substrate 250 and covers a portion of the opposite side of the microfluidic substrate 250. An integrated circuit (IC) device 272 is mounted on the control circuitry portion of the flex-circuit assembly 258. In one embodiment, the IC device 272 is a memory device (e.g., EPROM) for storing program code and data. The heater 270 covers a separation column within the microfluidic substrate 250. Mounted to the heater 270 is a temperature sensor 274.

The flex-circuit assembly 258 is constructed of multiple stacked layers (e.g., three, four, or five). The polymer substrate of each layer holds different interconnectivity or circuitry. One of the layers contains resistive traces of the heater 270. Electrical contacts at the two ends of the resistive traces connect to two pads 259 on the control circuitry portion 257. Another layer of the flex-circuit assembly 258 has vias that electrically contact the ends of the resistive traces, another layer has contacts to connect electrically to electrical components 272, 274, and still another layer has the pogo-pin contact pads 226 (FIG. 13). Through the flex-circuit assembly 258, each of the electrical components 272, 274 and resistive traces are electrically coupled to the contact pads 226. The gas inlet port 225 opens into a well 276 that channels injected gas into a gas tube 278 that delivers the gas to the emitter end 204.

Figure 15:
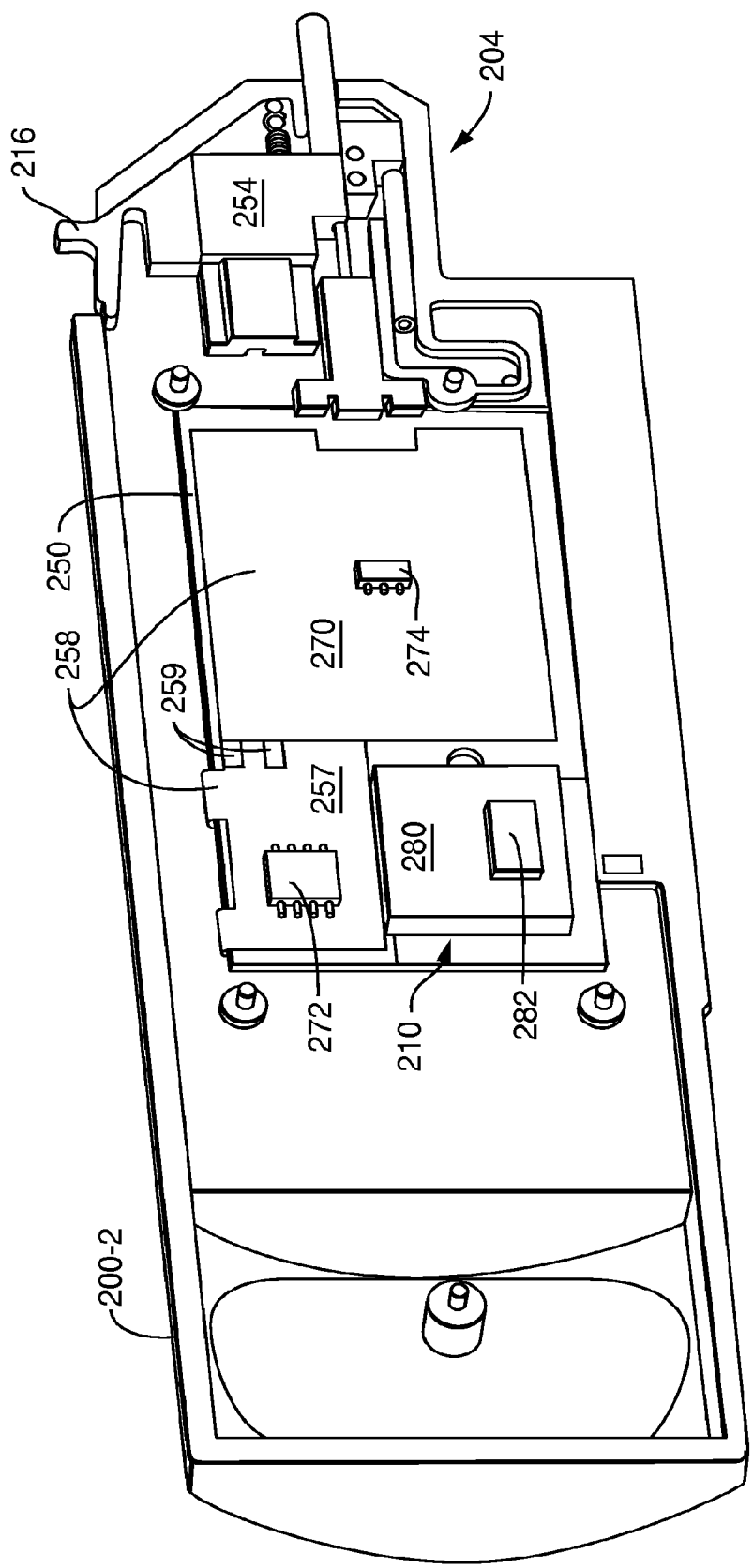
FIG. 15 is another side view of the microfluidic cartridge with the right side removed, showing a push block superimposed upon the microfluidic substrate in the microfluidic cartridge.

FIG. 15 shows the right side view of the microfluidic cartridge 16 of FIG. 14, again with the right casing section removed, and with the additional feature of the push block 210 (FIG. 13) suspended at the approximate location where the push block 210 abuts the microfluidic substrate 250. The location is near the southwest quadrant of the microfluidic substrate 250, directly below the flex-circuit assembly 258 and behind the heater 270 (with respect to the emitter end 204 being the front of the microfluidic cartridge 16). The push block 210 comprises a smaller rectangular block 282 disposed upon, or an integral extension of, a larger rectangular block 280. The smaller rectangular block 282 is sized to closely fit within the window 208 (FIG. 13) of the right casing section 200-1.

Figure 16:
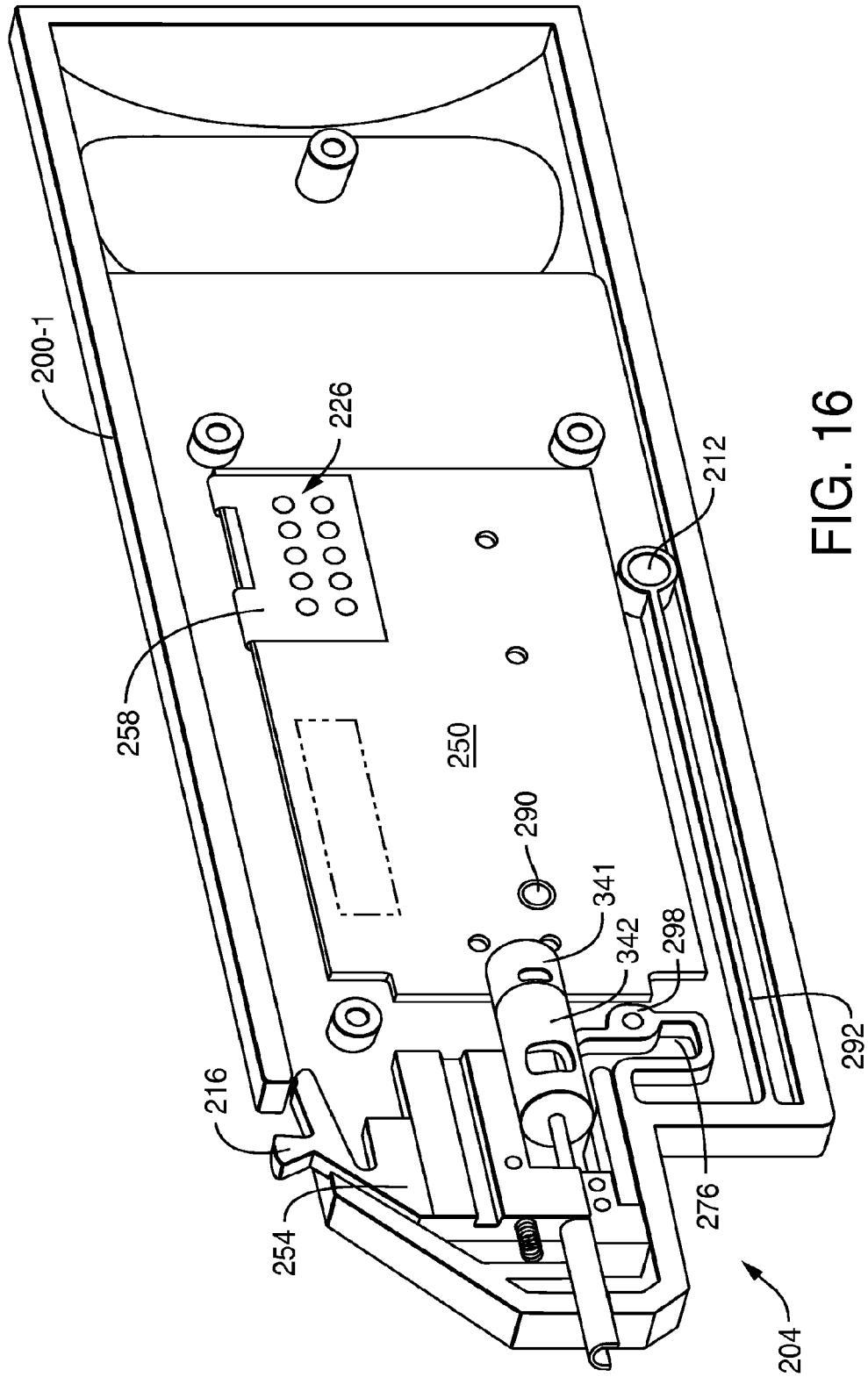
FIG. 16 is a side view of the microfluidic cartridge with the left side removed.

FIG. 16 shows a left side view of the microfluidic cartridge 16 with the left casing section removed to reveal various components housed within and to show features of the interior side of the right casing section 200-1. The flex-circuit assembly 258 wraps around onto this side of the microfluidic substrate 250, and includes the array of electrical contacts 226 of FIG. 12. In addition, the microfluidic substrate 250 has a high-voltage input port 290 for receiving the electrically conductive terminal of the high-voltage electrical cable 38 (FIG. 5). The high-voltage input port 290 is disposed near an egress end of a separation column within the microfluidic substrate 250, described below in connection with FIG. 17.

The interior side of the right casing section 200-1 includes a ridge 292 of casing material that runs from the emitter end 204 and terminates at the through-hole 212. When the casing sections 200-1, 200-2 are joined, the ridge 292 runs directly behind the groove 230 (FIG. 12) on the exterior side of the left casing section 200-2. The ridge 292 provides structural support to the microfluidic cartridge 16. In addition, by being directly opposite the groove 230, the ridge 292 resists bending of the cartridge 16 by the guide pin 128 (FIG. 7) should a user prematurely attempt to clamp the microfluidic cartridge 16 before the microfluidic cartridge 16 has fully reached the proper position. In addition, no portion of the microfluidic substrate 250 lies directly behind the groove 230, as a precautionary measure to avoid having the guide pin 128 bend the microfluidic substrate 250 in the event of a premature clamping attempt.

The interior side of the right casing section 200-1 provides the other half of the gas well 276, the walls of which align with and abut those defining the well 276 on the left casing section 200-2. To enhance a tight seal that constrains gas to within the gas well 276, a fastener or pin 296 (FIG. 14) tightens the connection between the casing sections at the opening 298 adjacent the well 276.

Figure 17:
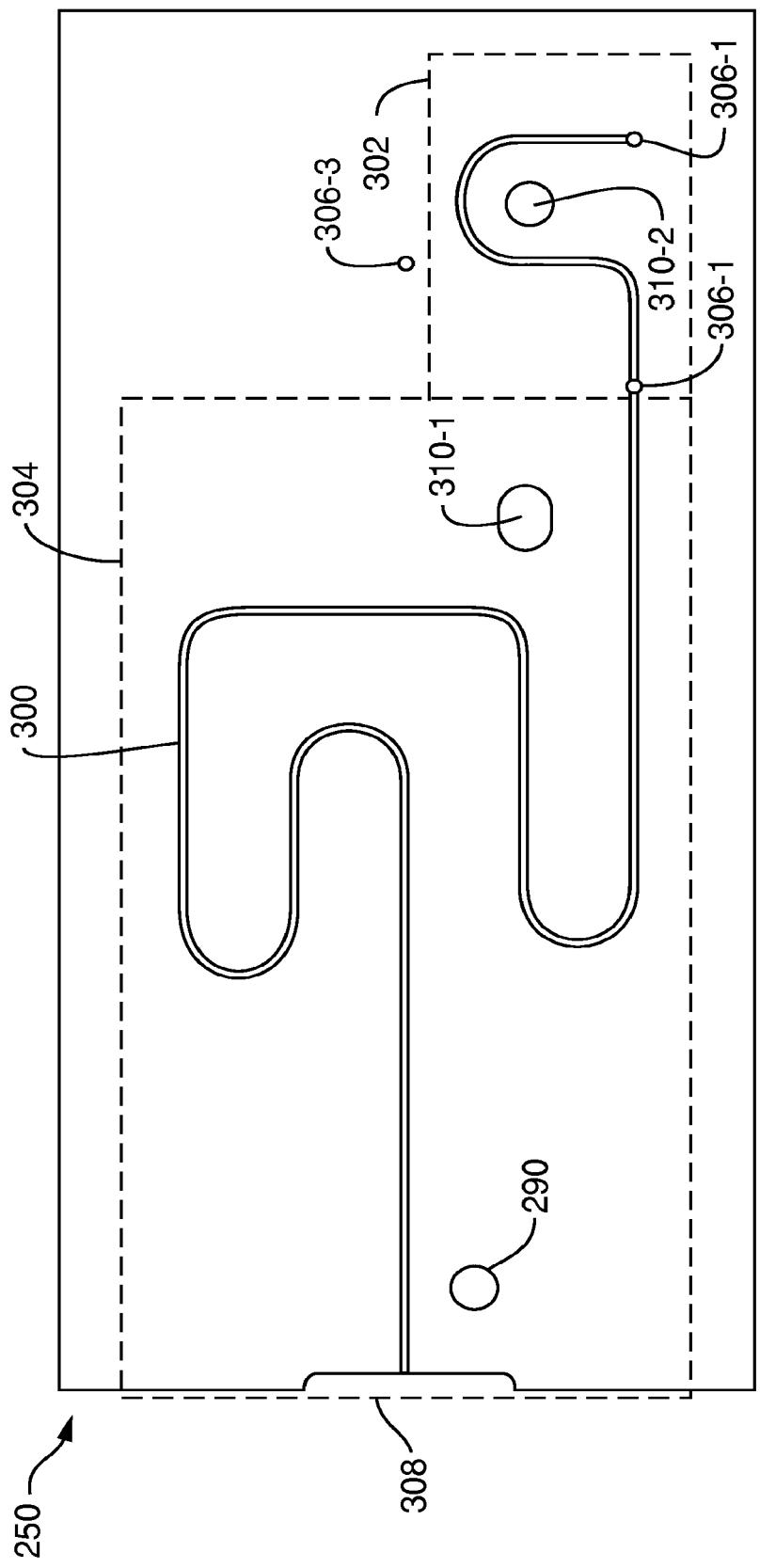
FIG. 17 is a side view of one embodiment of a microfluidic substrate within the microfluidic cartridge.

FIG. 17 shows a left side view of an embodiment of the microfluidic substrate 250. In brief overview, the microfluidic substrate 250 is generally rectangular, flat, thin (approx. 0.050"), and of multilayer construction. Formed within the layers of the microfluidic substrate 250 is a serpentine channel 300 for transporting liquid. The microfluidic substrate 250 includes a trap region 302 and a column region 304. In the embodiment shown, the microfluidic substrate 250 has three microscopic fluidic apertures 306-1, 306-2, 306-3 (generally 306). One of the fluidic apertures 306-1 intersects the channel 300 at one end of the trap region 302; another of the fluidic apertures 306-2 intersects the channel 300 at the other end of the trap region 302. In this embodiment, the third fluidic aperture 306-3 is unused. Alternatively, the third fluidic aperture 306-3 can be used, for example, as a calibration port; an operator can run a calibration fluid. The channel 300 terminates at an egress end of the microfluidic substrate 250. The fluidic aperture 306-2 at the "downstream" end of the trap region 302 is optionally used as a fluidic outlet aperture, for example, during loading of the trap region 302, and is optionally closed to fluid flow, for example, during injection of a loaded sample from the trap region 302 into the channel 300.

The microfluidic substrate 250 also has a high-voltage input port 290 (FIG. 16) and a pair of alignment openings 310-1, 310-2 (generally, 310) that each receives a peg that projects from an interior side of the left casing section 200-2. The alignment openings 310 help position the microfluidic substrate 250 within the microfluidic cartridge 16. The size of the alignment openings 310, with respect to the size of the pegs, allows the microfluidic substrate 250 some play within the microfluidic cartridge 16.

Figure 18:
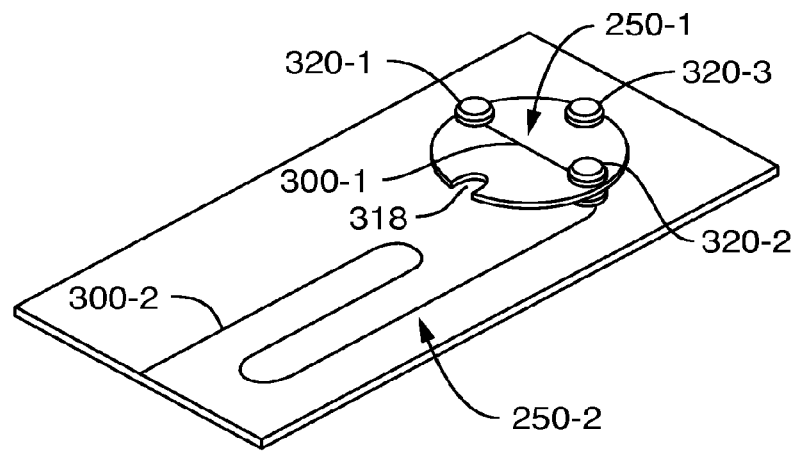
FIG. 18 is a view of another embodiment of a microfluidic substrate with self-alignment fittings.

Rather than a single microfluidic substrate 250, the microfluidic cartridge 16 can house a plurality of interconnected microfluidic substrates. FIG. 18 shows one embodiment with a plurality of the microfluidic substrates 250-1, 250-2 joined by fittings. The microfluidic substrates 250-1, 250-2 include a trap tile 250-1 coupled to a column tile 250-2. The trap tile 250-1 has a fluid-conducting channel 300-1 and the column tile 250-2 has a fluid conducting channel 300-2.

This embodiment of the trap tile 250-1 has three fluidic apertures (the open spot 318 in the tile 250-1 represents a possible embodiment having a fourth fluidic aperture). Coupled about each fluidic aperture is a fitting 320-1, 320-2, 320-3 (generally 320). The fittings 320 serve to self-align the tips of the nozzles (e.g., nozzles 130 or 184 of FIG. 7 or FIG. 10, respectively) on the fluidics block 90 when the microfluidic cartridge 16 is installed in the chamber, as described in more detail below. These fittings 310 can be made of metal, plastic, ceramic, or any combination of these materials. To couple the fittings 320 to the substrate 250-1, they can be glued, fastened, fused, brazed, or a combination thereof.

Figure 19:
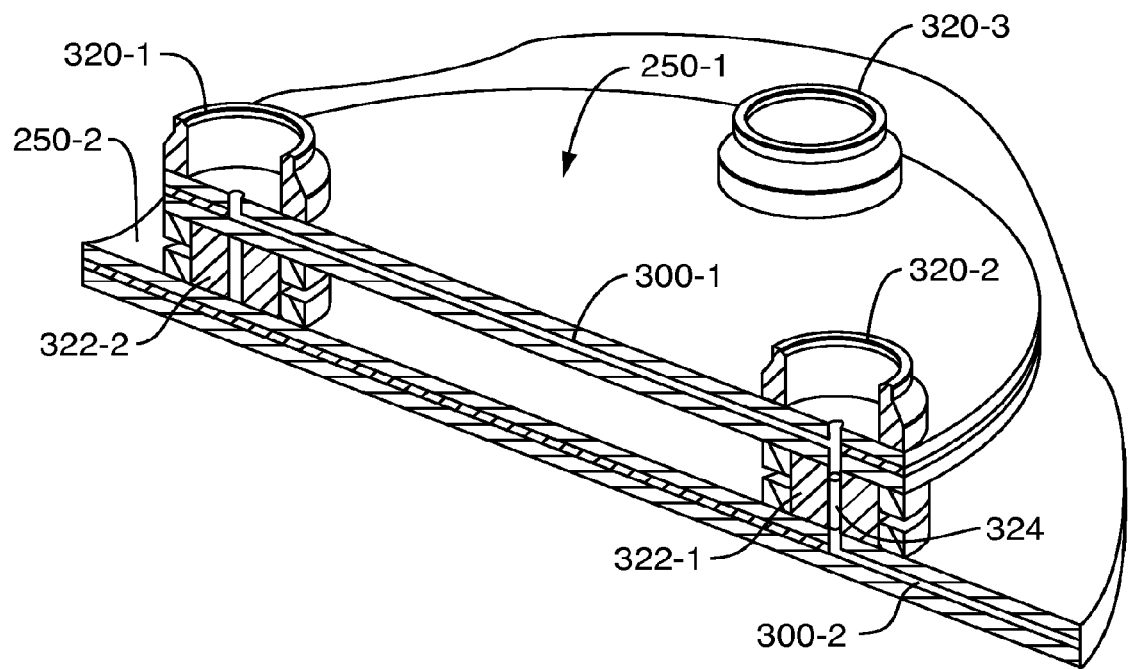
FIG. 19 is a cross-sectional view of the microfluidic substrate of FIG. 18.

FIG. 19 shows a cross-section of the trap tile 250-1 and column tile 250-2 that cuts through the fittings 320-1 and 320-2. The channel 300-1 of the trap tile 250-1 extends from the fitting 320-1 to the fitting 320-2. Couplers 322-1, 322-2 (generally, 322) connect the trap tile 250-1 to the column tile 250-2. Each coupler 322 is comprised of a pair of aligned fittings: one fitting on the underside of the trap tile 250-1, and the other fitting on the top side of the column tile 250-2. The coupler 322-1 provides a channel 324 for fluid passing through the channel 300-1 of the trap tile 250-1 to reach the channel 300-2 of the column tile 250-2. Like the fittings 320, the couplers 322 can be made of metal, plastic, ceramic, or any combination of these materials and can be glued, fastened, fused, and brazed, or any combination thereof, to the tiles 250-1, 250-2.

Preferably, the couplers 322 are formed of a deformable matter, for example, similar to or the same as the material of the nozzles 130; mechanical pressure alone can then provide a fluid-tight seal between the trap tile 250-1 and the couplers 322. Alignment-assisting features, such as the couplers 322, are optionally included in the embodiment illustrated in FIG. 17 and in other embodiments.

Figure 20:
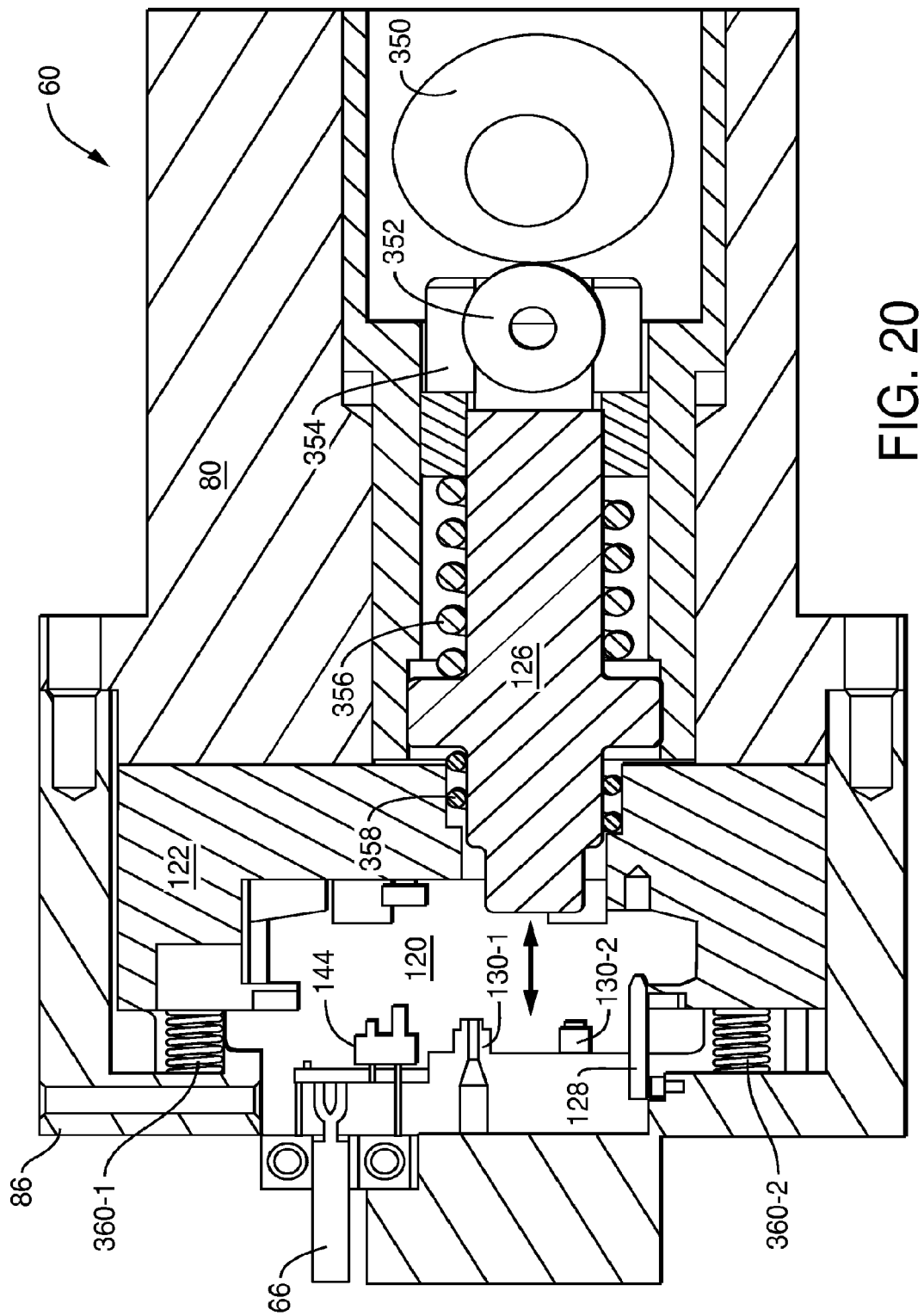
FIG. 20 is a cross-sectional front view of the clamping assembly without an installed microfluidic cartridge.
Figure 21:
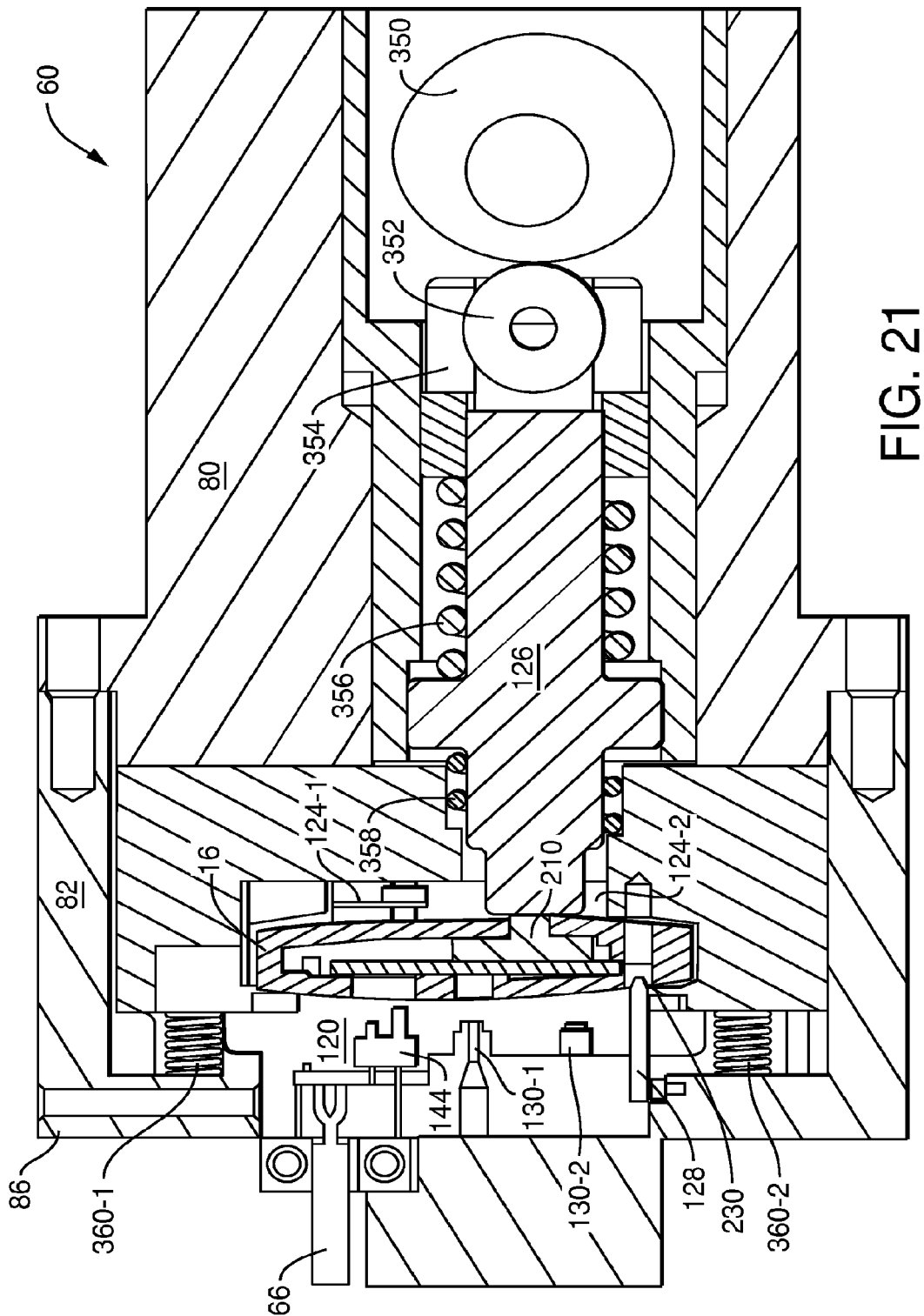
FIG. 21 is a cross-sectional front view of the clamping assembly with a microfluidic cartridge installed therein, and with the clamping assembly in an unclamped position.
Figure 22:
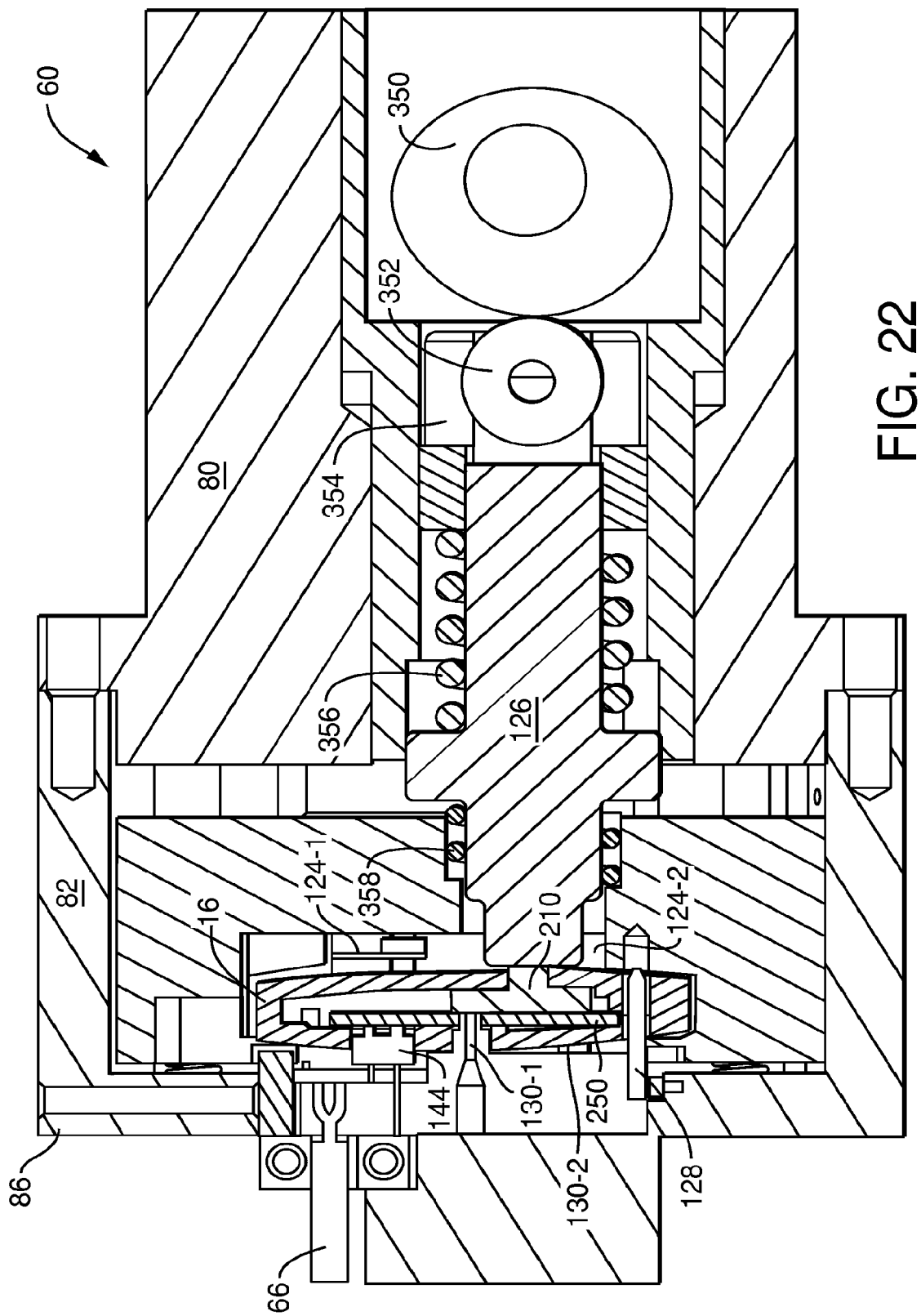
FIG. 22 is a cross-sectional front view of the clamping assembly with a microfluidic cartridge inserted therein, and with the clamping assembly in a clamped position.

FIG. 20, FIG. 21, and FIG. 22 illustrate the installation of a microfluidic cartridge 16 in the clamping assembly 60. FIG. 20 shows a cross-section of the clamping assembly 60 with an empty chamber 120; FIG. 21 shows the cross-section after insertion of the microfluidic cartridge 16 into the chamber 120, but before clamping; and FIG. 22 shows the cross-section after clamping. In each of FIG. 20, FIG. 21, and FIG. 22, the body 80 of the clamping assembly 60 houses a cam 350 and a cam follower 352. The cam follower 352 is within a carrier 354; a portion of the cam follower 352 extends beyond the carrier 354 and abuts the cam 350. One end of the plunger 126 is coupled to the cam follower 354 within the carrier 354. A load spring 356 wraps around a rearward section of the plunger 126, and a return spring 358 wraps around a forward section of the plunger 126. Optionally, in some embodiments, a cam is rotated to move a spring-loaded plunger into a closed position, and a secondary spring, such as the spring 358, provides load-balancing for more consistent and accurate introduction of a desired force, such as a force of 130 lbs.

In FIG. 20, the load spring 356 and return spring 358 are undamped; the lever 34 (FIG. 6), which is coupled to the cam 350, is in the open, unclamped position. In addition, springs 360-1, 360-2 (generally, 360) between the back wall 86 and the carriage 122 are likewise undamped. Projecting into the empty chamber 120, from the back wall of the end housing 82, are a pogo pin electrical connector 144, gas nozzles 130-1, 130-2 (a third nozzle being obscured), and the guide pin 128.

In FIG. 21, the microfluidic cartridge 16 is the chamber 120, with the emitter end of the cartridge entering the chamber 120 first. As the microfluidic cartridge 16 enters the chamber 120, the guide pin 128 slides along the groove 230 in the left casing section 200-2. When insertion of the microfluidic cartridge 16 into the chamber 120 reaches its limit, the plunger 126 abuts the push block 210 on the right side of the microfluidic cartridge 16, and the guide pin 128 reaches the through-hole 212 (FIG. 12) at the end of the groove 230. If the guide pin 128 is not aligned with this opening, the microfluidic cartridge 16 cannot be clamped. In one embodiment, the engagement of the arm 110 (FIG. 5) with the nook (FIG. 11) in the upper edge of the microfluidic cartridge 16 determines how far the microfluidic cartridge 16 can enter the chamber. In addition, the springs 124-1, 124-2 abut the right side of the microfluidic cartridge 16. As in FIG. 20, in FIG. 21 the load spring 356, the return spring 358, and the springs 360 are undamped because the lever 34 is in the open position.

In FIG. 22, the lever is closed, and the cam 350 causes the load spring 356 and return spring 358 to compress and urge the plunger 126 against the push block 210. The spaced-apart bosses 260 (FIG. 13) on the other side of the push block 210 distributes this force against the microfluidic substrate 250. The force against the push block 210 moves the carriage 122 and the microfluidic cartridge 16, together, towards the back wall 86 of the end housing 82. In addition, the spring 124-1 operates to push the microfluidic cartridge 16 downwards and toward the back wall 86, while springs 360-1, 360-2 (FIG. 21) compress, resisting the leftwards motion.

As a result of moving the carriage with the cartridge 16, the guide pin 128 penetrates the through-hole 212 in the microfluidic cartridge 16. The nozzles 130 that project inward from the back wall 86 enter the respective nozzle openings 220 (FIG. 12) in the left casing section of the microfluidic cartridge 16, and press against the surface of the microfluidic substrate 250. The urging force is sufficient to produce a sealed fluidic pathway between the each nozzle and the fluidic aperture. The clamping also causes the pogo pins 144 to enter the window 224 on the left casing section and make electrical connections with the array of electrical contacts 226.

Figure 23:
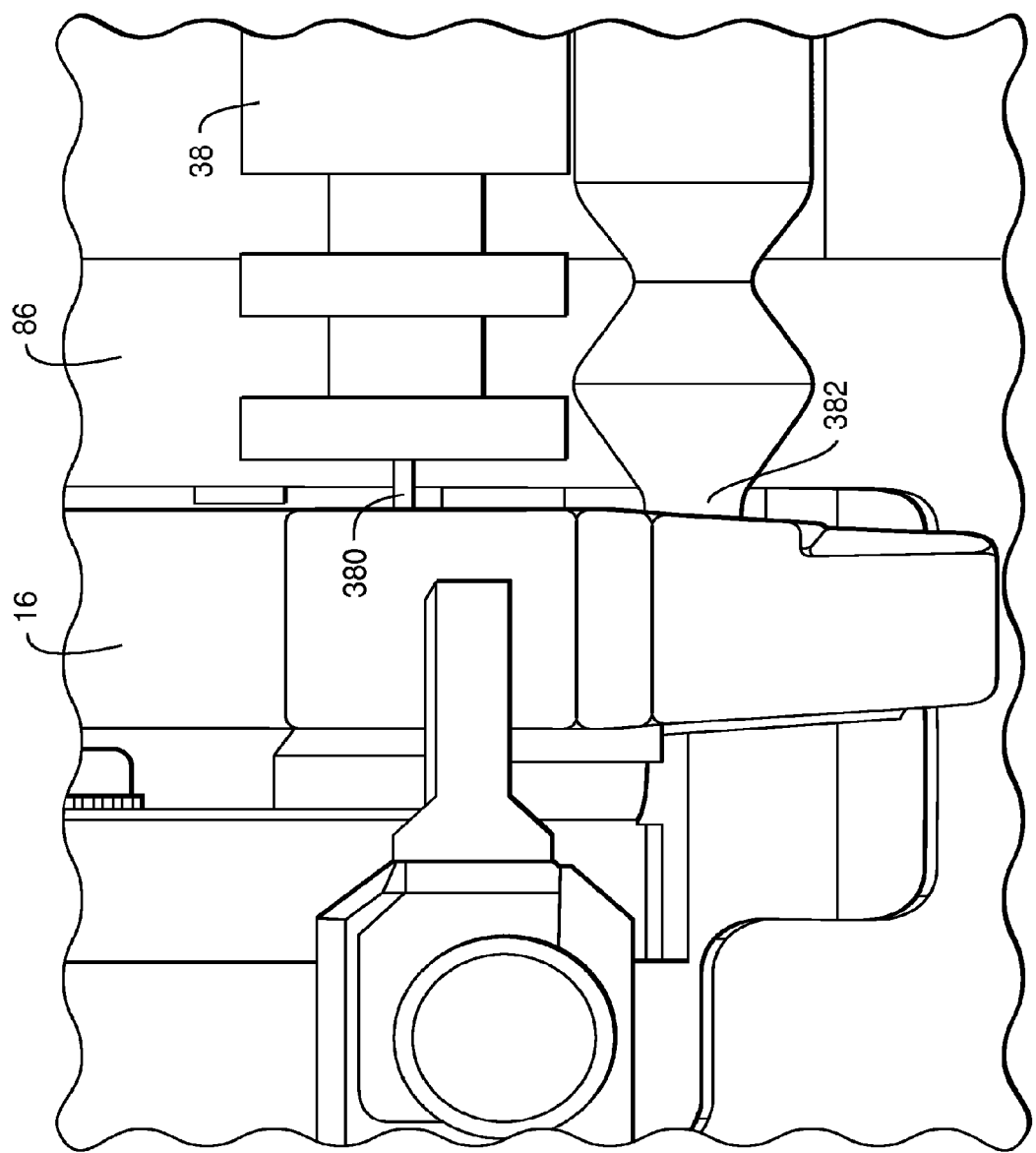
FIG. 23 is a view of the emitter end of the microfluidic cartridge, with a high-voltage cable and a gas nozzle coupled to a side thereof.

In addition to establishing the fluidic interface between the nozzles of the fluidic block and the microfluidic substrate, and the electrical interface between the pogo pins 144 and the array of electrical contacts 226, this clamping action also establishes (1) the electrical interface between the high-voltage pogo pin and the microfluidic substrate and (2) the fluidic interface between the gas nozzle and the microfluidic cartridge 16. FIG. 23 shows the high-voltage electrical cable 38 with a pogo pin 380 entering the left casing section of the microfluidic cartridge 16, and a gas nozzle tip 382 entering the gas inlet port of the left casing section.

While the invention has been shown and described with reference to specific preferred embodiments, it should be understood by those skilled in the art that various changes in form and detail may be made therein without departing from the scope of the invention as defined by the following claims.

What is claimed is:

1. A microfluidic device, comprising:
   i. a microfluidic substrate having a channel for transporting fluid, a first side of the microfluidic substrate having a plurality of apertures through which fluid is supplied to the channel and a second side of the microfluidic substrate opposite the first side, the channel disposed within the microfluidic substrate between the first and second sides;
   ii. an emitter assembly connected to the microfluidic substrate, said emitter assembly having an electrospray emitter including a lumen in communication with the channel at the second side of the microfluidic substrate; and
   iii. a housing enclosing the microfluidic substrate and at least a portion of the emitter assembly, the housing having a first side having a high-voltage input port configured to couple to a high-voltage cable, the housing further having a gas inlet port adapted to receive a gas nozzle for supplying a gas to the emitter assembly, and a plurality of nozzle openings each aligned with one of the apertures in the microfluidic substrate and adapted to receive a fluidic nozzle.

2. The microfluidic device of claim 1, further comprising circuitry including an electrical connector with an array of electrical contacts, wherein the circuitry further comprises a heater thermally coupled to the microfluidic substrate.

3. The microfluidic device of claim 1, further comprising a push block disposed proximate to the second side of the microfluidic substrate, the push block configured to press against the second side of the microfluidic substrate in response to an urging force applied to the push block.

4. The microfluidic device of claim 3, wherein the push block has at least three inwardly facing spatially separated bosses that press simultaneously against the second side of the microfluidic substrate in response to the urging force applied to the push block.

5. The microfluidic device of claim 4, wherein each of the at least three bosses aligns directly opposite one of the apertures in the first side of the microfluidic substrate.

6. The microfluidic device of claim 1, wherein the microfluidic substrate further comprises a separation column in fluidic communication with the channel.

7. The microfluidic device of claim 1, wherein the microfluidic substrate is formed of a ceramic-based material.

* * * * *